United States Patent
Thompson et al.

(10) Patent No.: US 7,468,160 B2
(45) Date of Patent: Dec. 23, 2008

(54) DEVICES AND METHODS FOR PERFORMING ARRAY BASED ASSAYS

(75) Inventors: Allen C. Thompson, Sunnyvale, CA (US); George P. Tsai, San Jose, CA (US); Russell Alan Parker, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 367 days.

(21) Appl. No.: 10/729,606

(22) Filed: Dec. 5, 2003

(65) Prior Publication Data

US 2005/0123931 A1    Jun. 9, 2005

(51) Int. Cl.
G01N 21/00 (2006.01)
G01N 15/06 (2006.01)
B01L 3/00 (2006.01)
C12M 1/34 (2006.01)
C12M 1/36 (2006.01)

(52) U.S. Cl. .................. 422/56; 422/68.1; 422/102; 422/58; 422/61; 435/287.9; 435/288.3; 435/286.5

(58) Field of Classification Search .................. 422/56, 422/61, 68.1, 102, 58; 435/287, 287.9, 286, 435/288.3, 286.5

See application file for complete search history.

(56) References Cited

U.S. PATENT DOCUMENTS 5,053,197 A * 10/1991 Bowen ..................... 422/58
5,958,760 A * 9/1999 Freeman .................. 435/286.5
6,258,593 B1   7/2001 Schembri et al.
6,399,394 B1   6/2002 Dahm et al.
6,623,701 B1 * 9/2003 Eichele et al. ............... 422/102
2004/0248318 A1 * 12/2004 Weinberger et al. ......... 436/173

OTHER PUBLICATIONS

U.S. Appl. No. 10/177,192, filed Jun. 21, 2002, entitled "Devices and Methods for Performing Array Based Assays."

* cited by examiner

Primary Examiner—Jill Warden
Assistant Examiner—Lore Ramillano

(57) ABSTRACT

Devices and methods for performing an array assay are provided. Embodiments of the subject array assay devices include (1) a base, (2) a cover, and (3) a clamping member for holding the cover to the base, wherein when the cover is operatively held to the base about a structure that includes an array assembly spaced-apart from a backing element, the array assembly and the backing element are deflected to substantially the same curvature. Embodiments of the subject methods include contacting a sample with a backing element and placing the backing element supported sample in contact with an array assembly to form a structure that includes the backing element and array assembly. The structure is then held together using a subject array assay device and the array substrate and the backing element are deflected to substantially the same curvature.

11 Claims, 16 Drawing Sheets

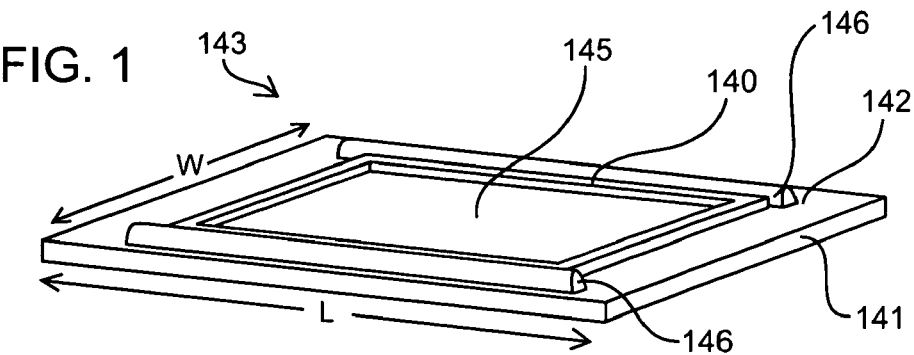
FIG. 1
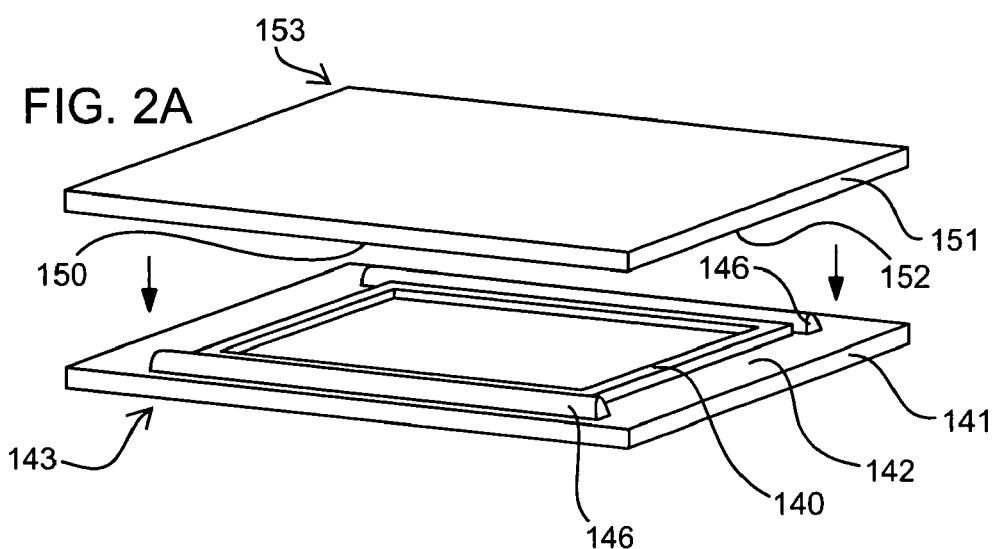
FIG. 2A
FIG. 2B
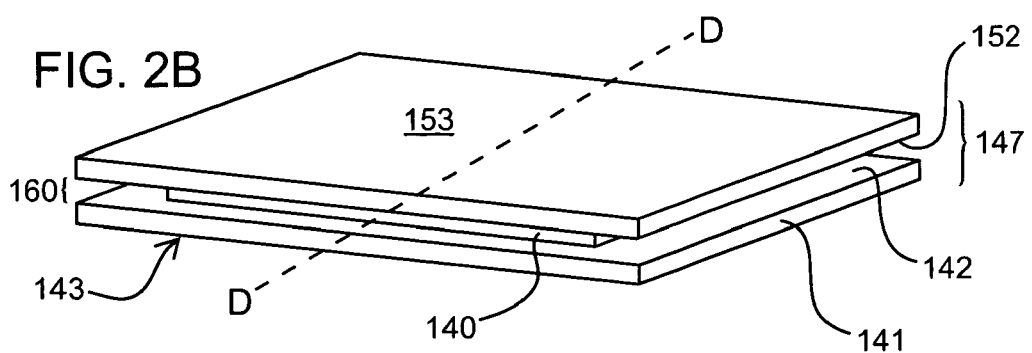
FIG. 2C
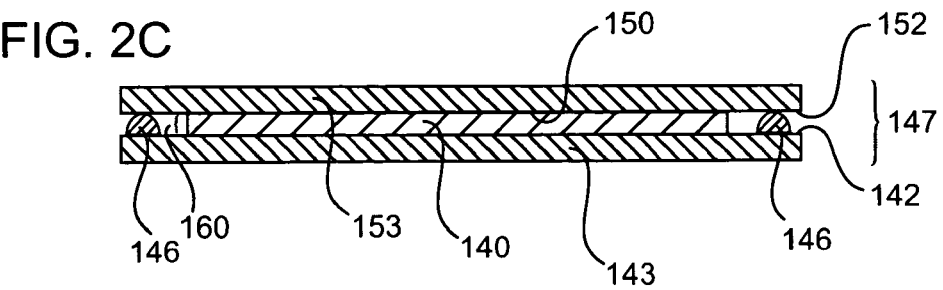

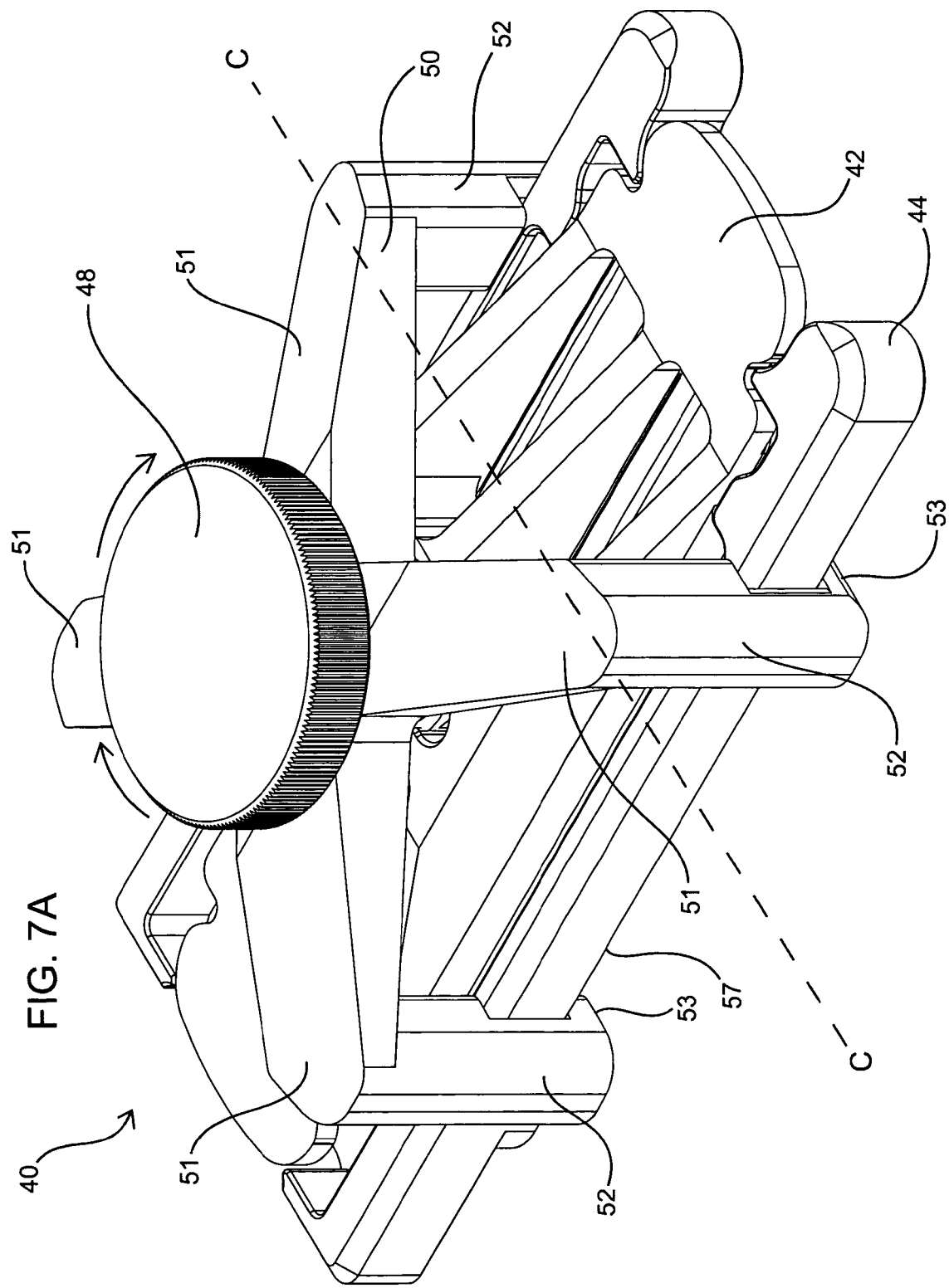

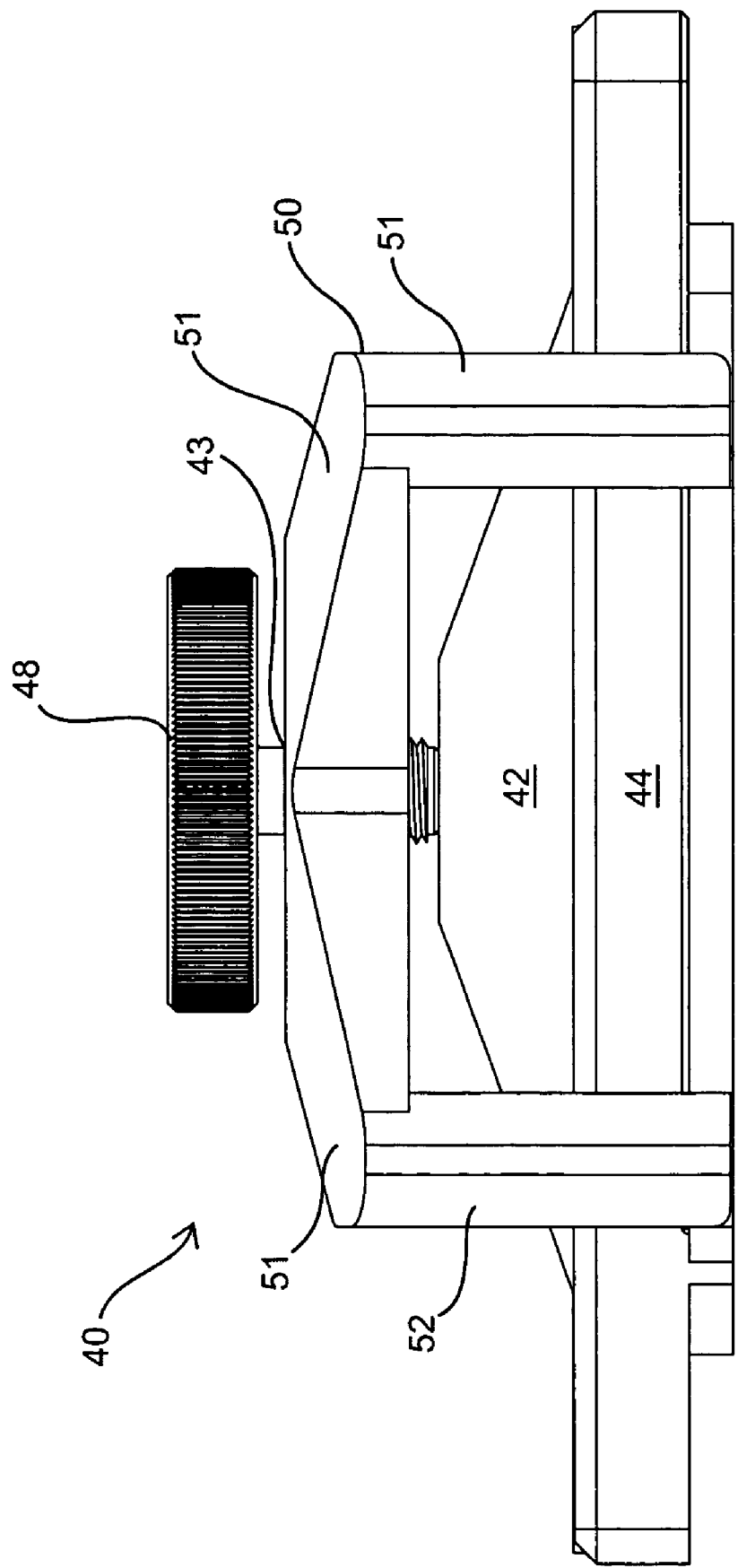

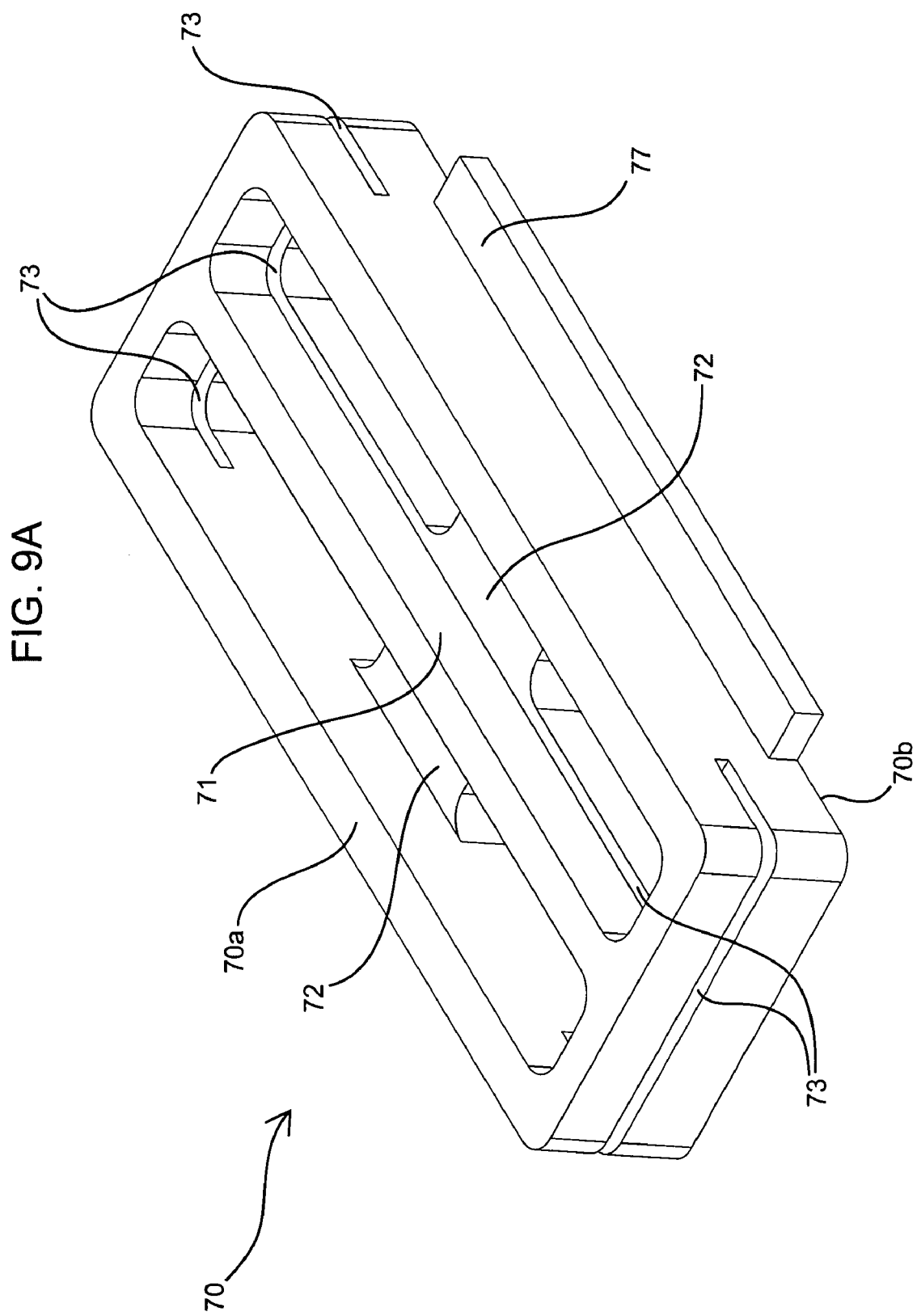

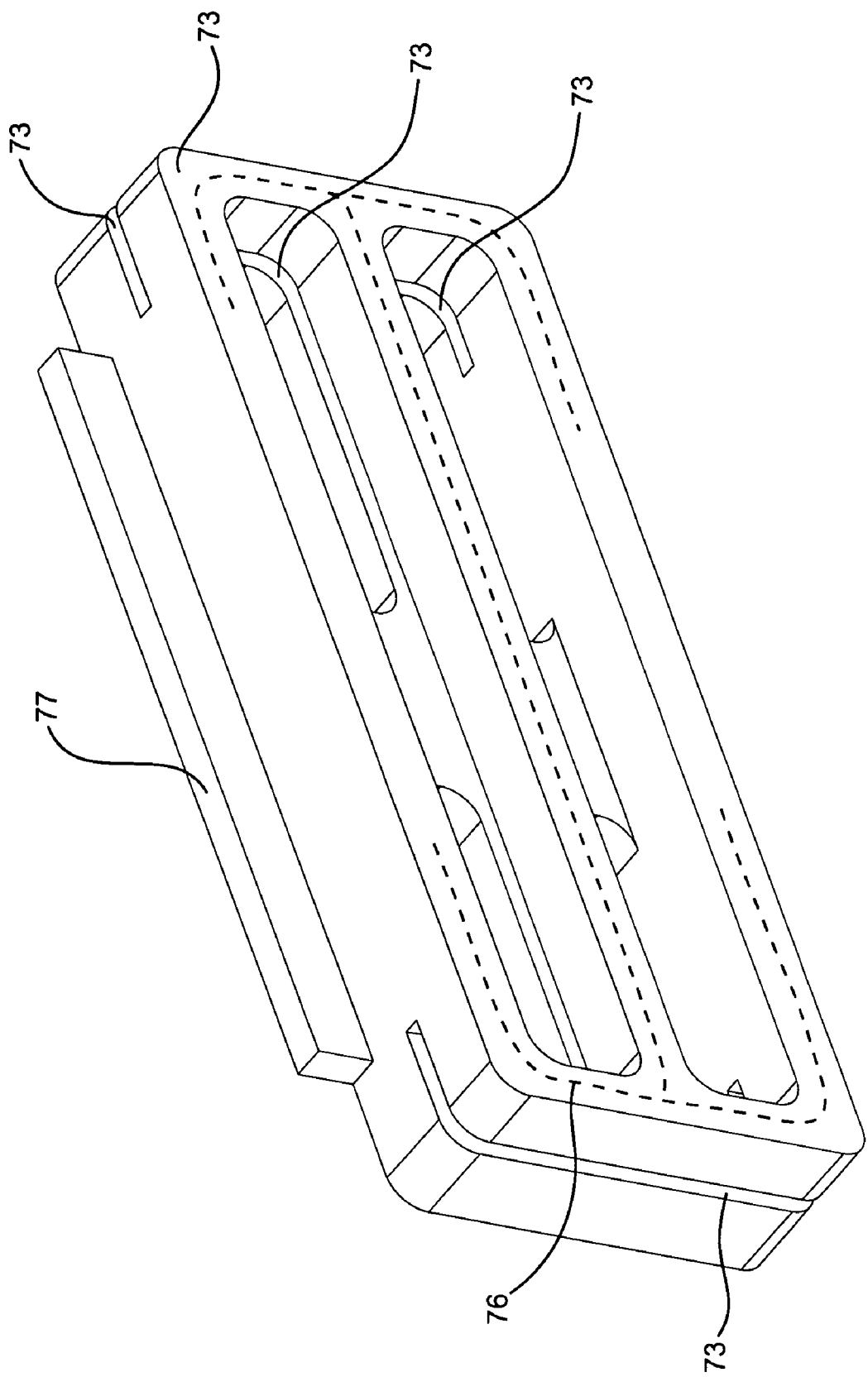

SECTION B-B

SECTION A-A

Force vs. Spring Deflection

DEVICES AND METHODS FOR PERFORMING ARRAY BASED ASSAYS

FIELD OF THE INVENTION

The field of this invention is biopolymeric arrays.

BACKGROUND OF THE INVENTION

Array assays between surface bound binding agents or probes and target molecules in solution may be used to detect the presence of particular biopolymers. The surface-bound probes may be oligonucleotides, peptides, polypeptides, proteins, antibodies or other molecules capable of binding with target molecules in solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.) and proteomics.

One typical array assay method involves biopolymeric probes immobilized in an array on a substrate such as a glass substrate or the like. A solution containing analytes that bind with the attached probes is placed in contact with the array substrate, covered with another substrate such as a coverslip or the like to form an assay area and placed in an environmentally controlled chamber such as an incubator or the like. Usually, the targets in the solution bind to the complementary probes on the substrate to form a binding complex. The pattern of binding by target molecules to biopolymer probe features or spots on the substrate produces a pattern on the surface of the substrate and provides desired information about the sample. In most instances, the target molecules are labeled with a detectable tag such as a fluorescent tag, chemiluminescent tag or radioactive tag. The resultant binding interaction or complexes of binding pairs are then detected and read or interrogated, for example by optical means, although other methods may also be used. For example, laser light may be used to excite fluorescent tags, generating a signal only in those spots on the biochip that have a target molecule and thus a fluorescent tag bound to a probe molecule. This pattern may then be digitally scanned for computer analysis.

As will be apparent, control of the assay environment and conditions contributes to increased reliability and reproducibility of the array assays. However, merely placing a substrate such as a coverslip over the array, as is commonly done, is often insufficient to allow precise control over the assay and permits leakage and evaporation of sample from the array site, where in many instances the quantity of sample is extremely limited.

During an array assay such as a hybridization assay, the assay is often performed at elevated temperatures and care must be taken so that the array does not dry out. Simply positioning a second slide over the array allows contents to leak or dry out during use, adversely impacting the assay. In addition, the substrate carrying the array cannot be tipped or moved from the horizontal position without risk that the substrate or cover slip will slip off. Maintaining the array in a humid environment may reduce drying-out, but offers only an incomplete solution.

Various closeable chambers or containers have been developed for conducting array-based assays which attempt to solve the problem of sample evaporation. However, many of these chambers fail to provide a complete seal around the array assay area. As such, leakage and evaporation of contents from the chamber still exists in these chambers. Furthermore, many of these chambers are complex and have numerous components that must be assembled by the user. Due to this complexity, the assembly process is often time-consuming and labor intensive.

Thus, there continues to be an interest in the development of new devices for array-based assays and methods of using the same. Of particular interest is the development of an array assay device, and methods of use thereof, that provides a fluid barrier around the assay area to prevent leakage and evaporation from the array assay area, is easy to assemble and use, includes a minimum of components, and that may also be capable of testing multiple samples with multiple arrays without cross-contamination.

SUMMARY OF THE INVENTION

Devices and methods for performing an array assay are provided. Embodiments of the subject array assay devices include (1) a base, (2) a cover, and (3) a clamping member for holding the cover to the base, wherein when the cover is operatively held to the base about a structure that includes an array assembly spaced-apart from a backing element, the array assembly and the backing element are deflected to the substantially the same curvature when the clamping member is operatively actuated. The subject devices provide a number of significant advantages including improved uniformity of the capillary distance provided between the held array assay assembly and array backing element as compared to conventional devices.

Embodiments of the subject methods include contacting a sample with a first surface of a backing element to produce a backing element supported sample and placing the backing element supported sample in contact with an array assembly including at least one array to form a structure that includes the backing element and array assembly. The structure is then held together using a subject array assay device and the array assembly and the backing element are deflected to the substantially the same curvature when the clamping member is operatively actuated. Once the array assay is complete, the at least one array may then be read to obtain a result.

Also provided are systems and kits for use in practicing the subject methods. The subject devices and methods find use in any array assay application, including genomic and proteomic array assay applications.

BRIEF DESCRIPTIONS OF THE DRAWINGS

FIG. 1 shows an exemplary embodiment of a backing element that may be employed with the subject array assay devices.

FIGS. 2A-2C show an exemplary embodiment of an array assay device that may be provided about one or more arrays using a backing element and an array assembly.

Figure 3A:
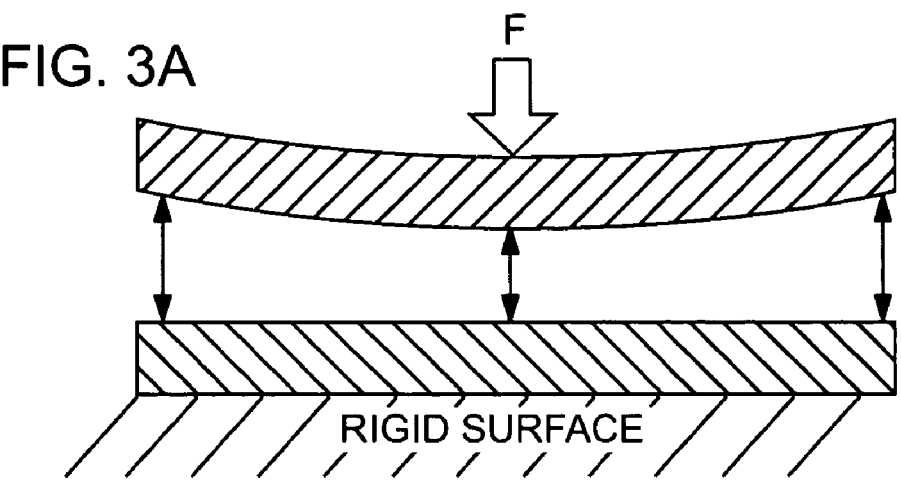
Figure 3B:
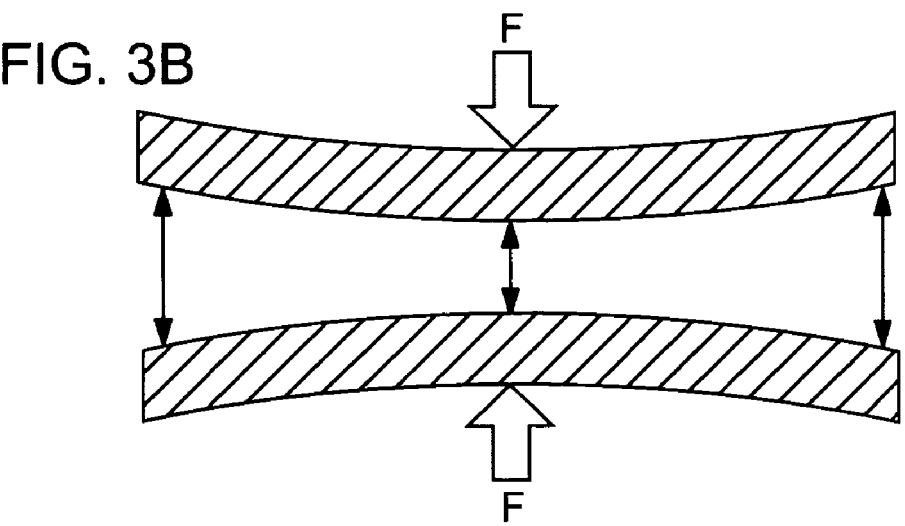

FIGS. 3A and 3B schematically show cross-sectional views of problems that may be encountered with many conventional array assay devices.

Figure 4:
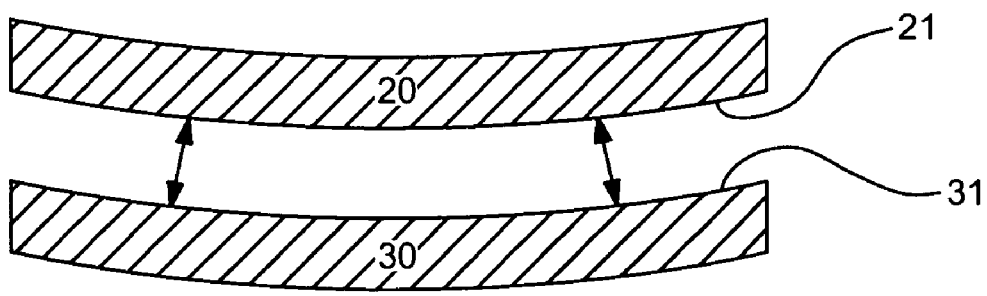

FIG. 4 shows a schematically illustrated cross-sectional view of an exemplary cover and base according to the subject invention in an operatively clamped configuration such that they are urged in substantially the same direction.

Figure 5A:
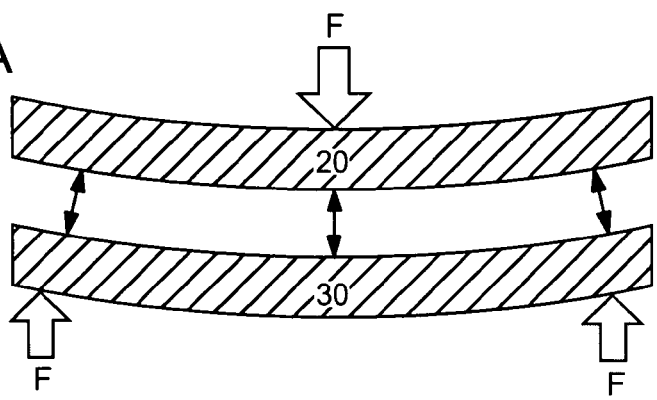
Figure 5B:
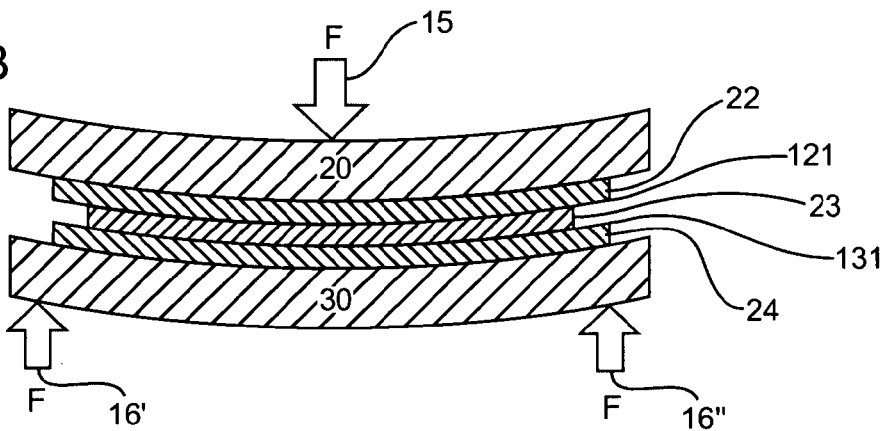

FIGS. 5A and 5B schematically illustrate a cover and a base urged in substantially the same direction according to the subject invention and the substantially uniform distance provided between the cover and the base of a subject array assay device (FIG. 5A) and between a backing element and array assembly (FIG. 5B) provided by the application of forces thereto in accordance with the subject invention.

Figure 6A:
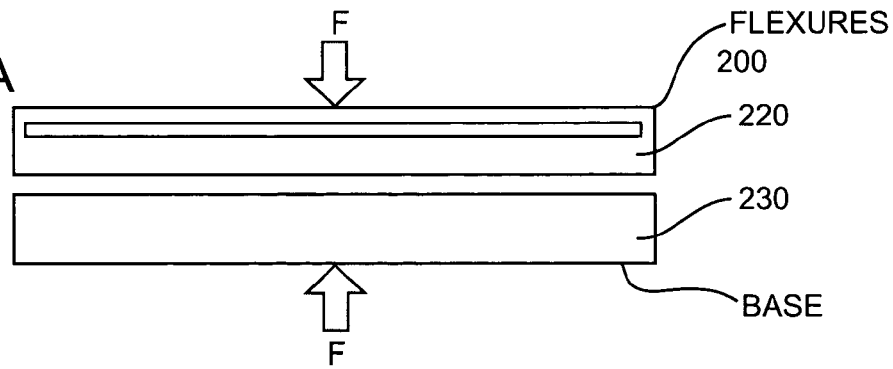
Figure 6B:
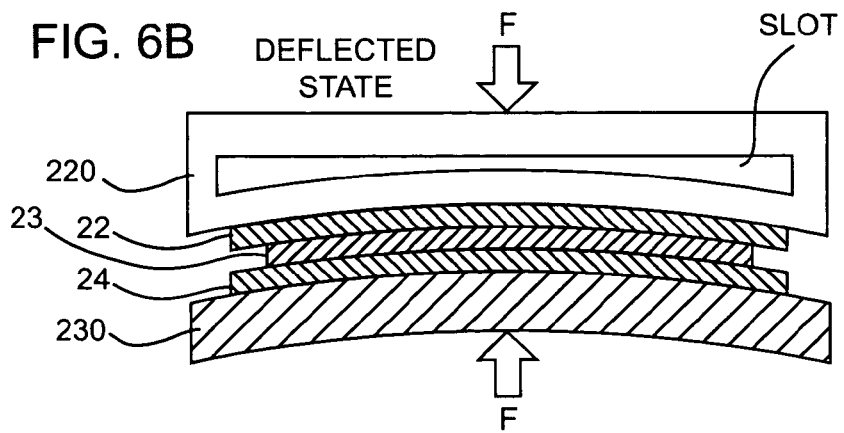

FIGS. 6A and 6B schematically illustrate an exemplary embodiment of an array assay device flexure cover in accordance with the subject invention.

FIGS. 7A-7F show exemplary embodiments of array assay devices according to the subject invention.

Figure 8:
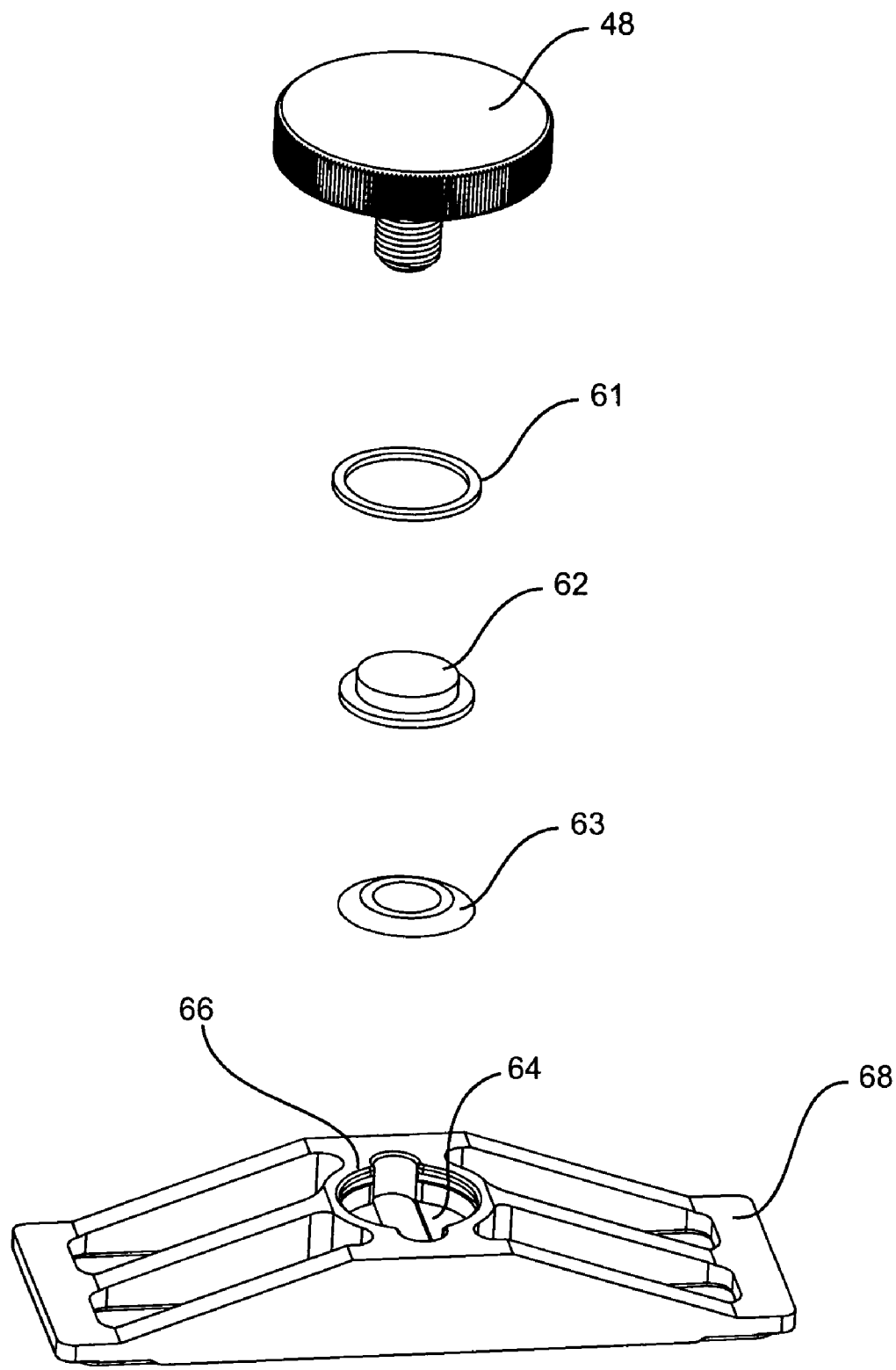

FIG. 8 shows an exemplary embodiment of an array assay device cover that includes at least one disk spring for use in a Disk Spring array assay device according to the subject invention.

FIGS. 9A-9F show an exemplary embodiment of an array assay flexure cover for use in a Flexure Cover array assay device according to the subject invention. FIG. 9G shows another exemplary embodiment of an array assay flexure cover for use in a Flexure Cover array assay device according to the subject invention.

Figure 10:
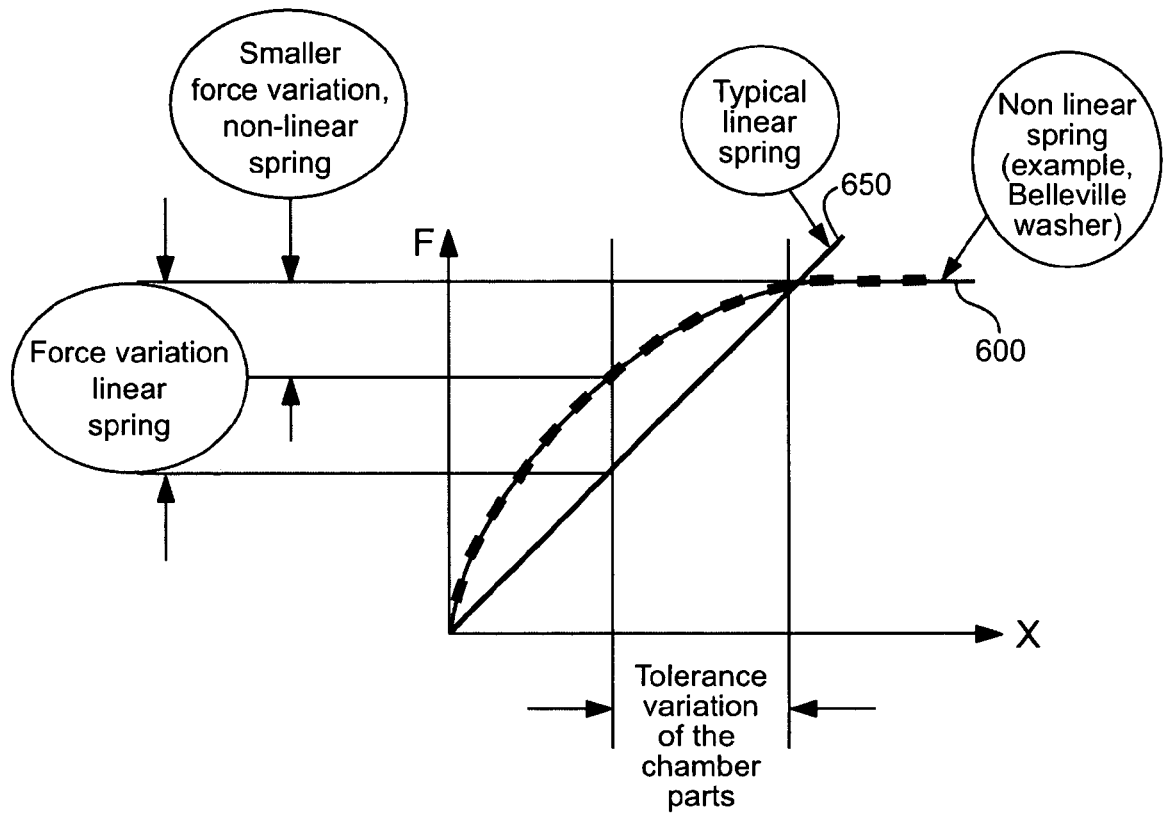

FIG. 10 shows a force vs. spring deflection graph for a typical liner spring and for a non-linear spring.

DEFINITIONS

The term "polymer" refers to any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "monomer" as used herein refers to a chemical entity that can be covalently linked to one or more other such entities to form an oligomer. Examples of monomers include nucleotides, amino acids, saccharides, peptides, and the like. In general, the monomers used in conjunction with the present invention have first and second sites (e.g., C-termini and N-termini, or 5' and 3' sites) suitable for binding to other like monomers by means of standard chemical reactions (e.g., condensation, nucleophilic displacement of a leaving group, or the like), and a diverse element which distinguishes a particular monomer from a different monomer of the same type (e.g., an amino acid side chain, a nucleotide rigid bottom cover surface, etc.). The initial substrate-bound monomer is generally used as a building-block in a multi-step synthesis procedure to form a complete ligand, such as in the synthesis of oligonucleotides, oligopeptides, and the like.

The term "oligomer" is used herein to indicate a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure.

The term "ligand" as used herein refers to a moiety that is capable of covalently or otherwise chemically binding a compound of interest. The ligand may be a portion of the compound of interest. The term "ligand" in the context of the invention may or may not be an "oligomer" as defined above. The term "ligand" as used herein may also refer to a compound that is synthesized on the substrate surface as well as a compound is "pre-synthesized" or obtained commercially, and then attached to the substrate surface.

The terms "array," "biopolymeric array" and "biomolecular array" are used herein interchangeably to refer to an arrangement of ligands or molecules of interest on a substrate surface, which can be used for analyte detection, combinatorial chemistry, or other applications wherein a two-dimensional arrangement of molecules of interest can be used. That is, the terms refer to an ordered pattern of probe molecules adherent to a substrate, i.e., wherein a plurality of molecular probes are bound to a substrate surface and arranged in a spatially defined and physically addressable manner. Such arrays may be comprised of oligonucleotides, peptides, polypeptides, proteins, antibodies, or other molecules used to detect sample molecules in a sample fluid.

The term "biomolecule" means any organic or biochemical molecule, group or species of interest that may be formed in an array on a substrate surface. Exemplary biomolecules include peptides, proteins, amino acids and nucleic acids.

The term "peptide" as used herein refers to any compound produced by amide formation between a carboxyl group of one amino acid and an amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g., deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA"s used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

The term "sample" as used herein relates to a material or mixture of materials, typically, although not necessarily, in fluid form, containing one or more components of interest.

The terms "nucleoside" and "nucleotide" are intended to include those moieties which contain not only the known purine and pyrimidine rigid bottom cover surfaces, but also other heterocyclic rigid bottom cover surfaces that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "chemically inert" is used herein to mean the chemical structure is substantially unchanged by contact with reagents and conditions normally involved in array based assays such as hybridization reactions or any other related reactions or assays, e.g., proteomic array applications.

The term "communicating" information refers to transmitting data representing that information as electrical signals over a suitable communication channel (for example, a private or public network).

The term "forwarding" an item refers to any means of getting that item from one location to the next, whether by physically transporting that item or otherwise (where that is possible) and includes, at least in the case of data, physically transporting a medium carrying the data or communicating the data.

The term "physically inert" is used herein to mean the physical structure is substantially unchanged by contact with reagents and conditions normally involved in array based assays such as hybridization reactions or any other related assays or reactions.

The terms "target" "target molecule" and "analyte" are used herein interchangeably and refer to a known or unknown molecule in a sample, which will hybridize to a molecular probe on a substrate surface if the target molecule and the molecular probe contain complementary regions, i.e., if they are members of a specific binding pair. In general, the target molecule is a biopolymer, i.e., an oligomer or polymer such as an oligonucleotide, a peptide, a polypeptide, a protein, and antibody, or the like.

The term "hybridization" as used herein refers to binding between complementary or partially complementary molecules, for example as between the sense and anti-sense strands of double-stranded DNA. Such binding is commonly non-covalent binding, and is specific enough that such binding may be used to differentiate between highly complementary molecules and others less complementary. Examples of highly complementary molecules include complementary oligonucleotides, DNA, RNA, and the like, which comprise a region of nucleotides arranged in the nucleotide sequence that is exactly complementary to a probe; examples of less complementary oligonucleotides include ones with nucleotide sequences comprising one or more nucleotides not in the sequence exactly complementary to a probe oligonucleotide.

The term "hybridization solution" or "hybridization reagent" used herein interchangeably refers to a solution suitable for use in a hybridization reaction.

The terms "mix" and "mixing" as used herein means to cause fluids to flow within a volume so as to more uniformly distribute solution components, as after different solutions are combined or after a solution is newly introduced into a volume or after a component of the solution is locally depleted.

The term "probe" as used herein refers to a molecule of known identity adherent to a substrate.

The term "remote location" refers to a location other than the location at which the array is present and hybridization occur. As such, when one item is indicated as being "remote" from another, what is meant is that the two items are at least in different buildings, and may be at least one mile, ten miles, or at least one hundred miles apart.

The term "stringent hybridization conditions" as used herein refers to conditions that are compatible to produce duplexes on an array surface between complementary binding members, i.e., between probes and complementary targets in a sample, e.g., duplexes of nucleic acid probes, such as DNA probes, and their corresponding nucleic acid targets that are present in the sample, e.g., their corresponding mRNA analytes present in the sample. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate. Stringent hybridization conditions are hybridization conditions that are at least as stringent as the above representative conditions. Other stringent hybridization conditions are known in the art and may also be employed.

DETAILED DESCRIPTION OF THE INVENTION

Devices and methods for performing an array assay are provided. Embodiments of the subject array assay devices include (1) a base, (2) a cover, and (3) a clamping member for holding the cover to the base, wherein when the cover is operatively held to the base about a structure that includes an array assembly spaced-apart from a backing element, the array assembly and the backing element are deflected to the substantially the same curvature when the clamping member is operatively actuated. The subject devices provide a number of significant advantages including improved uniformity of the capillary distance provided between the held array assay assembly and array backing element as compared to conventional devices.

Embodiments of the subject methods include contacting a sample with a first surface of a backing element to produce a backing element supported sample and placing the backing element supported sample in contact with an array assembly including at least one array to form a structure that includes the backing element and array assembly. The structure is then held together using a subject array assay device and the array assembly and the backing element are deflected to the substantially the same curvature when the clamping member is operatively actuated. Once the array assay is complete, the at least one array may then be read to obtain a result.

Also provided are systems and kits for use in practicing the subject methods. The subject devices and methods find use in any array assay application, including genomic and proteomic array assay applications.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "an array" includes a plurality of such arrays and reference to "the fluid barrier" includes reference to one or more fluid barriers and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

Introduction

As summarized above, the subject invention provides devices and methods for performing array-based assays, i.e., array binding assays. The subject invention may be employed with a number of different types of arrays in which a plurality of distinct polymeric binding agents (i.e., of differing sequence) are stably associated with at least one surface of a substrate or solid support. The polymeric binding agents may vary widely, however polymeric binding agents of particular interest include peptides, proteins, nucleic acids, polysaccharides, synthetic mimetics of such biopolymeric binding agents, etc. In certain embodiments of interest, the biopolymeric arrays are arrays of nucleic acids, including oligonucleotides, polynucleotides, cDNAs, mRNAs, synthetic mimetics thereof, and the like. Exemplary representative arrays that may be used with the subject invention are described in greater detail below.

While the subject devices and methods find use in array hybridization assays, the subject devices and methods also find use in any suitable binding assay in which members of a specific binding pair interact. That is, any of a number of different binding assays may be performed with the subject devices and methods, where typically a first member of a binding pair is stably associated with the surface of a substrate and a second member of a binding pair is free in a sample, where the binding members may be: ligands and receptors, antibodies and antigens, complementary nucleic acids, and the like. For ease of description only, the subject devices and methods described below will be described primarily in reference to hybridization assays, where such examples are not intended to limit the scope of the invention. It will be appreciated by those of skill in the art that the subject devices and methods may be employed for use with other binding assays as well, such as immunoassays, proteomic assays, etc.

In further describing the subject invention, the subject array assay devices are described first in greater detail, followed by a review of the subject methods and representative applications in which the subject methods find use. Finally, kits that find use in practicing the subject methods are described.

Array Assay Devices

As summarized above, the subject invention includes array assay devices for performing array assays, i.e., assays with biopolymeric arrays. Embodiments of the subject array assay devices include a housing for use in performing array assay protocols. Embodiments of the subject array assay device housings include a base and a cover which, when in a closed orientation about an array assembly/backing element structure positioned therebetween, deflects the array assembly and the backing element to substantially the same curvature. Embodiments also include devices configured to provide a substantially uniform capillary gap or distance between an array assembly and a backing element held by the device. For example, certain embodiments include one or more spacers that limit the travel of a device cover and/or base and/or array assembly and/or backing element, when the clamping member is operatively actuated to provide a compression force. In such embodiments, a compression force is applied all along the length of the spacer(s) positioned therebetween, all along the hardstop contacting surfaces, etc., to provide a uniform capillary gap between the array assembly and backing element. In other words, embodiments of the subject array assay devices provide compression forces to the cover and base of the housing which in turn deflects a backing element and array assembly positioned within the housing to substantially the same curvature, e.g., substantially the same direction, along the entire lengths of the backing element and array assembly contacting surfaces.

Accordingly, the subject array assay devices are dimensioned to fit with a structure that includes (1) a backing element that includes a backing element substrate and at least one gasket (also referred to herein as a fluid retaining structure) positioned on a surface thereof, and (2) an array assembly that includes an array substrate having at least one array positioned on a surface of the array substrate. In use, the backing element and array substrate are positioned in opposition to each other with the at least one gasket positioned therebetween and the structure (i.e., the array substrate/backing element structure) is positioned between the cover and base of a subject array assay device. A clamping member of the array assay device is used to hold, i.e., clamp, the base and the cover together about the backing element/array assembly structure in a manner to deflect the backing element and array assembly in substantially same shape or curvature when the clamping member is tightened or rather operatively clamped or actuated. Embodiments include array assay devices configured to provide a substantially uniform distance between the array assembly and backing element at least about an array of the array assembly when the clamp is engaged about the backing element/array assembly structure. In certain embodiments, the subject array assay devices are configured to apply opposing forces, e.g., equally opposing forces, to the backing element and array assembly to compress them together in a manner analogous to that described above. Before further describing the subject devices, a review of exemplary, representative embodiments of array backing elements and array assemblies is first provided to provide a proper foundation for the subject array assay devices.

Exemplary Representative Array Backing Elements

Embodiments of array backing elements that may be used with the subject invention include a solid substrate having at least one substrate surface, upon which is positioned at least one fluid retaining structure (also herein referred to as a gasket), where in certain embodiments a plurality of fluid retaining structures may be present on the substrate surface such that a plurality of fluids such as samples may be retained in each of the fluid retaining structures without cross-contamination of the fluids. A gasket may be fixedly attached to a backing element substrate or may be a readily separable component, i.e., not fixedly attached. In accordance with the subject invention, each subject fluid retaining structure is configured to hold and effectively retain a volume of fluid such as a volume of a fluidic sample, e.g., for use in an array assay protocol such as an analyte detection protocol. Representative array backing elements are disclosed, e.g., in U.S. application Ser. No. 10/172,850, the disclosure of which is herein incorporated by reference.

As note above, an array backing element includes a solid substrate. The substrate of an array backing element may assume a variety of shapes and sizes, where they are typically configured (e.g., sized, shaped, etc.) to be operatively associated or joined with another substrate (i.e., an array substrate) having at least one array thereon to provide an array assay chamber, as will be described in greatera detail below. At least one surface of a backing element substrate is usually planar, but in certain embodiments may deviate from planar, e.g., portions of a backing element substrate surface may be nonplanar (e.g., may include recessed structures, elevated structures, channels, orifices, guides, and the like).

Typically, the particular shape of a subject backing element substrate is dictated at least in part by the array assembly with which it may be used such that the shape of a given backing element substrate is one which corresponds or "fits" with an array assembly. In any event, the shapes of these backing element substrates range from simple to complex. In many embodiments, the substrates may assume a square, rectangular, oblong, oval or circular shape, etc., as well as other geometric shapes and irregular or complex shapes.

Likewise, the size of the subject backing element substrates may vary depending on a variety of factors, including, but not limited to, the number of fluid retaining structures present thereon, the particular array assembly to which it is to be joined, etc. Generally, the subject backing element substrates are sized to be easily transportable or moveable. For example, the backing element substrate may be shaped generally as a rectangle (although other shapes are possible, e.g., circular, etc.), having a length that may range from about 4 mm to about 1 m, usually more than about 4 mm to about 600 mm, more usually less than about 400 mm, e.g., the length may range from about 15 mm to about 40 mm, e.g., from about 20 mm to about 35 mm, e.g., from about 20 mm to about 30 mm; a width that may range from about 4 mm to about 1 m, usually less than about 500 mm and more usually less than about 400 mm, e.g., the width may range from about 15 mm to about 40 mm, e.g., from about 20 mm to about 35 mm, e.g., from about 20 mm to about 30 mm; and a thickness that may range from about 0.01 mm to about 5.0 mm, e.g., from about 0.02 to about 2 mm, e.g., 0.02 to about 1.5 mm, e.g., about 0.1 mm to about 1.5 mm. Certain embodiments include backing elements designed to be used with array assemblies having dimensions of about 1 inch by 3 inches. Accordingly, such backing elements may have analogous dimensions to those of the 1 inch by 3 inch array assembly. Shapes other than rectangular may have analogous dimensions.

Backing element substrate materials are chosen to provide sufficient physical support for one or more fluid retaining structures positioned on at least one surface of the backing element substrate and are also chosen to endure the conditions of any treatment or handling or processing that may be encountered in the use of the substrate, array assays, e.g., hybridization assays, protein binding assays, etc. One or more materials may be used to fabricate the backing element substrates such that a plurality of materials may be employed. Examples of materials which may be used to fabricate the subject substrates include, but are not limited to, metals such as stainless steel, aluminum, and alloys thereof, polymers, e.g., plastics and other polymeric materials such as poly (vinylidene fluoride), poly(ethyleneterephthalate), polyurethane, e.g., nonporous polyurethane, fluoropolymers such as polytetrafluoroethylene (e.g., Teflon®), polypropylene, polystyrene, polycarbonate, PVC, nylon, and blends thereof, siliceous materials, e.g., glasses, fused silica, ceramics and the like.

The backing element substrates may also be fabricated from a "composite," i.e., a composition made up of different or unlike materials. The composite may be a block composite, e.g., an A-B-A block composite, an A-B-C block composite, or the like. Alternatively, the composite may be a heterogeneous combination of materials, i.e., in which the materials are distinct from separate phases, or a homogeneous combination of unlike materials. As used herein, the term "composite" is used to include a "laminate" composite. A "laminate" refers to a composite material formed from several different bonded layers of identical or different materials.

As described above, the backing element substrates include at least one fluid retaining structure present on at least one surface of the substrate. The fluid retaining structures may be any suitable structure that retains a fluid. For example, in certain embodiments the one or more fluid retaining structures present on a substrate surface may include a material that changes from a first fluid state to a second solid state in response to a stimulus and include Form in Place Gaskets described in U.S. patent application Ser. No. 10/010,945, the disclosure of which is herein incorporated by reference. However, it is to be understood that other suitable fluid retaining structures may be employed. For example, a fluid retaining structure may be formed at a location other than on a backing element substrate and then transferred to the backing element substrate at some time prior to using the backing element in an array assay. In any event, in certain embodiments multiple, discrete fluid retaining structures may be present on a backing element substrate surface so that multiple samples, which may be the same or different, to be applied to a single backing element substrate (i.e., to each fluid retaining structure), without cross-contamination of the samples.

FIG. 1 shows an exemplary embodiment of a backing element that may be employed with the subject array assay devices. As shown, a backing element 143 includes fluid retaining structure 140 that is disposed around and marks the perimeter of an interior area 145 on surface 142 of a backing element substrate 141. The interior area and the fluid retaining structure thus define a well-like or container structure that is adapted for retaining a fluid, where the well-like structure is defined by the walls of the fluid retaining structure and the backing element substrate surface that is bounded or enclosed by the fluid retaining structure (i.e., the interior area). The shape of the interior area may be altered depending on the desired use, e.g., by altering the configuration of the fluid retaining structures and/or substrate surface, and the like.

The shape of a fluid retaining structure will depend on a variety of factors such as the particular array feature or spot it is intended to encompass. As such, the subject fluid retaining structures may assume a variety of different shapes such that the shapes of these structures range from simple to complex. In many embodiments, the fluid retaining structures will assume a square, rectangular, oblong, oval or circular shape, although other shapes are possible as well, such as other geometric shapes, as well as irregular or complex shapes. In certain embodiments, the width or diameter of a fluid retaining structure may not be constant throughout the entire thickness or height of the structure, i.e., the width may vary. Accordingly, shapes such as cone-like, spiral, helical, pyramidal, parabolic, frustum, etc., are possible as well.

Typically, the number of fluid retaining structures present on a backing element substrate may range from about 1 to about 100 or more, for example as many as about 3, 6, 8, 20, 48, and 96 or more fluid retaining structures may be present on a single substrate. As such, the configuration or pattern of fluid retaining structures may vary depending on the particular array assay to be performed, the number of fluid retaining structures present, the size and shape of the fluid retaining structures present, the size, shape and pattern of the arrays to which the fluid retaining structures are to be joined, etc. For example, the pattern of the fluid retaining structures may be in the form of a grid or other analogous geometric or linear pattern or the like, e.g., analogous to a conventional microtiter plate grid pattern and in certain embodiments the fluid retaining structures are present in a non grid-like or non-geometric pattern.

The physical dimensions of a subject fluid retaining structure may be characterized in terms of thickness, and/or width, and/or length (e.g., length may be used for structures having non-round shapes). Thickness or height is defined as the perpendicular distance from the substrate surface to most distal (i.e., top) surface of the fluid retaining structure. The width of a fluid retaining structure is defined as the internal width of a fluid retaining structure. The length is defined as the long axis of the fluid retaining structure that is parallel to the plane of the substrate surface. In structures having round or round-like (e.g., oblong, etc.) shapes, the length may be analogous to a major axis. In those embodiments having more than one fluid retaining structure, it is to be understood that the dimensions (and/or the shapes and/or materials) of the fluid retaining structures may be the same or some or all of the fluid retaining structures may have different dimensions (and/or shapes and/or materials).

The dimensions of a fluid retaining structure are such that any fluid retaining structure is able to accommodate a volume of fluid sufficient to perform an array assay, i.e., able to retain a sufficient volume of sample for an array assay. Typically, the fluid retaining structures or the wells formed thereby (defined by the surface of the substrate on which it is positioned and the fluid barrier walls), will contain a volume of fluid of at least about 1-500 µl or more, where the volume may range from about 1 µl to about 5000 µl or more, e.g., from about 5 µl to about 1000 µl, e.g., from about 10 µl to about 1000 µl, where the volume may be as great as about 1000 µl to about 5000 µl or greater in certain embodiments. Embodiments include fluid retaining structures that can accommodate a volume of fluid that ranges from about 40 µl to about 500 µl.

The thickness or height of a fluid retaining structure is of a dimension that is suitable to retain a sufficient amount of sample for an array assay. Accordingly, a fluid retaining structure may have a height or thickness of at least about 5 to about 10 micrometers, e.g., at least about 15 micrometers in certain embodiments, e.g., at least about 20 micrometers in certain embodiments, where in certain embodiments the height may be about 25 micrometers to about 100 micrometers or more or even up to about 250 micrometers or more, where the height may be up to about 500 micrometers or more, even up to about 1000 micrometers or up to about 5000 micrometers or more, where the height may be a few millimeters or more in certain embodiments. The length may be at least about 20 to about 50 micrometers or more, e.g., may be at least about 20 to about 500 micrometers or more, e.g., may be at least about 1000 micrometers or more, e.g., may be at least about 1500 micrometers to about 2500 micrometers or more, where in certain embodiments the width may be up to about 3000 micrometers or more, e.g., up to about 4000 micrometers or more or even up to about 5000 micrometers or more in certain embodiments, even up to about 7000 micrometers or even up to about 10,000 micrometers or more in some embodiments. The width may range up to about 1.5 mm, sometimes up to about 3 mm, and sometimes up to about 6 mm in certain embodiments. The width of a fluid retaining structure, defined by the internal width, may vary, where the width may be at least about 200 to about 500 micrometers, e.g., may be at least about 1000 micrometers or more, e.g., may be at least about 1500 micrometers to about 2500 micrometers or more, where in certain embodiments the width may be up to about 3000 micrometers or more, e.g., up to about 4000 micrometers or more or even up to about 5000 micrometers or more in certain embodiments, even up to about 7000 micrometers or even up to about 10000 micrometers or more in some embodiments. For example, the width may range up to about 1.5 mm or more, sometimes up to about 3 mm or more, and sometimes up to about 20 mm or more in certain embodiments.

The fluid retaining structure material(s) is selected to provide a fluid retaining structure having particular properties, e.g., suitable thickness, structure and fluid retaining properties, stability, inertness, array assay protocol compatibility, etc. The subject fluid retaining structures may be flexible or deformable upon application of a suitable force thereto or may be rigid, i.e., not easily deformable or not deformable at all upon application of a suitable force thereto.

The fluid retaining structure may be made of any suitable material. In certain embodiments, a fluid retaining structure includes a material that changes from a first fluid state to a second solid state in response to a stimulus. In other words, the fluid retaining structure if formed by employing a suitable curing protocol and as such the material of the fluid retaining structures may correctly be characterized as a curable material. In other words, the material of the fluid retaining structures may be transformed or otherwise altered or changed from a fluid state to a solid state in response to a stimulus, where the transformation, alteration or change from the fluid state to the solid state is irreversible. The subject fluid retaining structures may be changed from a first fluid state to a second solid state prior to or after being positioned at an intended location on a backing element substrate surface such that in certain embodiments the fluid retaining structure is formed (i.e., changed from a first fluid state to a second solid state) "in place" on an array backing element substrate and in certain other embodiments the fluid retaining structure is formed at a first location which is a location other than on a surface of a backing element substrate upon which it will ultimately be positioned and then transferred to a backing element substrate. Regardless of how a particular fluid retaining structure is fabricated, the solid state or solid form of a fluid retaining structure is suitable for retaining a fluid within its boundaries and suitable for use in an array protocol.

Any material having suitable characteristics (e.g., for retaining a fluid, for use in an array assay, etc.) may be used as a fluid retaining structure material. Suitable fluid retaining structure material may derive from naturally occurring materials, naturally occurring materials that have been synthetically modified, or synthetic materials. Fluid retaining structures materials are generally fluid materials that may be cured to provide a solid fluid retaining structure having suitable characteristics. Selection of a fluid retaining structure material is determined relative to the intended application. Suitable fluid retaining structure materials include, but are not limited to polymers, elastomers, silicone sealants (e.g., Loctite 5964 thermal cure silicone), urethanes, and polysulfides, latex, acrylic, etc. In certain embodiments, the fluid retaining structure material is a fluoropolymer such as polytetrafluoroethylene, e.g., a Teflon® such as a liquid Teflon®, e.g., Teflon® AF which is from a family of amorphous fluoropolymers provided by E.I. du Pont de Nemours and Company. In certain embodiments the fluid retaining structure includes a polymer that is an elastomer (e.g., polyisoprene, polybutadiene, polyisobutylene, polyurethanes, and the like).

In certain embodiments, after the fluid retaining structure material is deposited in a fluid form in the predetermined configuration either at the desired site on a backing element substrate surface or at another location (e.g., a non-backing element substrate), the fluid retaining structure material is changed or transformed or rather is cured to form a fluid retaining structure that is solid by the application of a suitable stimulus thereto. Any suitable stimulus may be employed, where various stimuli are known in the art for changing a fluid material to a solid material. Accordingly, various methods of curing are available and may be utilized with the subject invention, the choice of which depends on a variety of factors such as the particular fluid retaining structure material(s) used, i.e., the particular properties of the material(s), the amount of time available for curing, etc.

The backing elements may also include one or more optional spacers or bumpers 146. The optional spacers may be positioned on the surface of a backing element substrate that includes the one or more fluid retaining structures and are usually, though not always, positioned along the lengths of the substrate (i.e., as opposed to the widths), as indicated in FIG. 1 as "L" for length and "W" for width. As noted above, the spacers serve to ensure that a uniform spacing is provided between the backing element and an array assembly when the two are operably clamped together using a subject array assay device, as will be described in greater detail below. Alternatively, or in addition to the one or more optional spacers, hardstop tabs and corresponding ledges may be provided (see for example FIG. 7B), e.g., hardstop tabs on a cover which are dimensioned to fit with corresponding ledges on a base, or vice versa. The spacers and hardstop tabs/ledges serve analogous functions to assist in keeping the distance between a backing element and array assembly uniform when positioned within a subject array assay device.

As described in greater detail below, the subject invention provides novel devices and methods to control the clamping force applied to an array assembly/backing element structure.

Exemplary Representative Array Assemblies

As described above, a backing element may be employed with an array assembly that includes an array substrate having at least one array to provide an array assay chamber about the at least one array. The array assay chamber may then be used in a variety of different array assay protocols as will be described in greater detail below. Specifically, a backing element may be positioned adjacent an array assembly and specifically an array substrate such that the one or more backing element gaskets are operatively positioned between a surface of the backing element substrate and a surface of the array substrate about at least one array.

Arrays (also known as microarrays) include at least two distinct polymers that differ by monomeric sequence attached to different and known locations on the microarray substrate surface. Each distinct polymeric sequence of the array is typically present as a composition of multiple copies of the polymer on a substrate surface, e.g., as a spot or feature on the surface of the substrate. The number of distinct polymeric sequences, and hence spots or similar structures, present on the array may vary, where a typical array may contain more than about ten, more than about one hundred, more than about one thousand, more than about ten thousand or even more than about one hundred thousand features in an area of less than about 20 cm$^2$ or even less than about 10 cm$^2$. For example, features may have widths (that is, diameter, for a round spot) in the range from about 10 μm to about 1.0 cm. In other embodiments, each feature may have a width in the range from about 1.0 μm to about 1.0 mm, usually from about 5.0 μm to about 500 μm and more usually from about 10 μm to about 200 μm. Non-round features may have area ranges equivalent to that of circular features with the foregoing width (diameter) ranges. At least some, or all, of the features are of different compositions (for example, when any repeats of each feature composition are excluded, the remaining features may account for at least about 5%, 10%, 20%, 30% or about 90% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents, but may not be present when, for example, photolithographic array fabrication process are used. It will be appreciated though, that the interfeature areas, when present, could be of various sizes and configurations. The spots or features of distinct polymers present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like.

In the broadest sense, the arrays are arrays of polymeric or biopolymeric ligands or molecules, i.e., binding agents, where the polymeric binding agents may be any of: peptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like.

The arrays may be produced using any convenient protocol. Various methods for forming arrays from pre-formed probes, or methods for generating the array using synthesis techniques to produce the probes in situ, including known light directed synthesis processes, are generally known in the art (see, for example, U.S. Pat. Nos. 6,180,351; 6,242,266; 6,306,599 and 6,420,180, the disclosures of which are incorporated herein by reference). For example, probes can either be synthesized directly on the array solid support or substrate or attached to the substrate after they are made. Arrays may be fabricated using drop deposition from pulse jets of either polynucleotide precursor units (such as monomers) in the case of in situ fabrication, or the previously obtained polynucleotide. Other drop deposition methods may be used for fabrication. Also, instead of drop deposition methods, photolithographic array fabrication methods may be used. As mentioned above, interfeature areas need not be present, particularly when the arrays are made by photolithographic methods as described in those patents. Accordingly, as described above, the probes may be synthesized directly on a substrate, or pre-made probes may be attached to the substrate, after the substrate has been modified according to the subject invention.

Immobilization of the probe to a suitable substrate may be performed using conventional techniques. See, e.g., Letsinger et al. (1975) Nucl. Acids Res. 2:773-786; Pease, A. C. et al., Proc. Nat. Acad. Sci. USA, 1994, 91:5022-5026, and Oligonucleotide Synthesis, a Practical Approach," Gait, M. J. (ed.), Oxford, England: IRL Press (1984). The surface of a substrate may be treated with an organosilane coupling agent to functionalize the surface. See, e.g., Arkins, A Silane Coupling Agent Chemistry," Petrarch Systems Register and Review, Eds. Anderson et al. (1987) and U.S. Pat. No. 6,258,454.

Any given array substrate may carry one, two, four or more arrays disposed on a surface of the substrate. Depending upon the use, any or all of the arrays may be the same or different from one another and each may contain multiple spots or features. For example, a plurality of arrays may be stably associated with one substrate, where the arrays are spatially separated from some or all of the other arrays associated with the substrate.

As shown in FIGS. 2A-2C, to provide an assay chamber about an array using a backing element and an array substrate having at least one array, herein shown as employing backing element 143 of FIG. 1. Accordingly, to provide an array assay chamber about at least one array of an array assembly, a backing element 143 having at least one gasket 140 positioned on a surface 142 of the backing element substrate 141, is positioned in opposition to an array assembly 153 having an array substrate 151 with one or more arrays 150 (not shown) on a surface 152 of substrate 151 such that gasket 140 of backing element 143 is facing and is in direct opposition to the surface 152 of array substrate 151 that has arrays 150 thereon, as shown in FIG. 2A. Backing element 143 and array assembly 153 are brought into sufficiently close proximity to "sandwich" the gasket between the two, as shown in FIG. 2B and FIG. 2C, where FIG. 2C shows a cross sectional view of the backing element and array assembly of FIG. 2B along lines D-D wherein gasket 140 is positioned therebetween. (Optional spacers 146 are omitted in FIG. 2B to provide a view of the sandwiched gasket, but are shown in FIG. 2C as optional spacers 146). In this manner, a structure 147 is provided that includes the backing element 143 and array assembly 153 and at least one gasket 140 therebetween about at least one array. An array assay chamber 160 is thus formed about the one or more arrays 150 by surface 152 of array assembly 153, surface 142 of backing element 143 and the walls of gasket 140.

To provide a sealed assay chamber, e.g., to prevent leakage of sample from the assay chamber, etc., the backing element and array assembly need to be maintained in a fixed position with the gasket held therebetween about at least one array. More specifically, the backing element and the array substrate need to be compressed together in order for a gasket disposed therebetween to provide a tight seal around an array. For example, inadvertent movement of one of the components, and/or if the gasket does not provide a tight seal, fluidic contents retained in the assay chamber may leak or evaporate which may adversely affect the array assay results. As noted above, the subject array assay devices are employed with a backing element/array assembly structure to maintain the structure in a fixed position and provide a tight seal about an array. A uniform capillary height (i.e., the distance between the backing element and array assembly), is also important for achieving a uniform signal from the array after an array assay, i.e., upon reading of the array following an array assay protocol. Accordingly, the subject array assay devices are configured to clamp a backing element/array assembly structure together to deflect the backing element and array structure in substantially the same shape or curvature along the entire length of the structure, i.e., along all the backing element and array assembly contacting surfaces.

FIGS. 3A and 3B schematically show cross-sectional views of problems that may be encountered with many conventional array assay devices. As shown, in order to hold a backing element/array assembly together in an operable position, a compression force, e.g., applied by an array assay device, may be applied to a backing element/array assembly structure, e.g., positioned in an array assay device, where the force provided by conventional array assay devices is applied to such a structure at a single point of the structure—either from a first side as shown in FIG. 3A or from first and second sides as shown in FIG. 3B. However, such does not deflect the backing element and array assembly in the same direction or to substantially the same shape as is desired. Accordingly, such conventional array assay device configurations may provide a non-uniform distance along the dimension of the structure, i.e., the distance or assay chamber height may be smallest at regions nearest the areas where the force(s) is applied and greater at distances further away from these regions, as shown in FIGS. 3A and 3B. Specifically, as shown the outer edges of the structure may become deflected in opposing directions and this deflection causes the distance between the backing element and array substrate to be greater at its ends than at the middle—or at the point where the force is applied. Such un-even or rather non-uniform distances between the array backing element and array assembly may adversely affect array assay results and/or cause the fluidic contents retained between the backing element and array structure in a fluid retaining structure to leak out. One solution to this problem is to increase the thickness and/or weight of one or both of the sides of the device. However, implementing this solution increases manufacturing costs and adds weight to the device.

In contrast to the above-described conventional array assay devices, embodiments of the subject array devices are configured to defelct a backing element and array assembly to substantially the same shape. Embodiments also provide improved control over the capillary gap provided therebetween relative to conventional array assay devices. As noted above, embodiments of the subject array assay devices provide a substantially uniform distance along the entire length dimension of the device, as shown for example in FIGS. 4, 5A, 5B, 6A and 6B, thus providing a substantially uniform distance, i.e., capillary gap, between a backing element and array assembly positioned between the cover and base. By "substantially uniform" is meant that the distance between a surface of an array substrate and an opposing surface of a backing element substrate, when a cover and a base of an array assay device is operatively clamped about the array substrate and backing element to hold them together, does not differ by more than about 1 micron to about 300 microns, e.g., not more than about 5 microns to about 100 microns, e.g., not more than about 10 microns to about 30 microns.

FIG. 4 shows a schematically illustrated cross-sectional view of an exemplary array assay device cover 20 and base 30 according to the subject invention in an operative clamped position (clamp member not shown). The deflection of the base and cover is exaggerated for illustrative purposes. As shown, the capillary gap (indicated by arrows between the cover and the base) between cover 20 and base 30 is substantially uniform along the entire lengths of the cover and base as the cover 20 and base 30 are deflected to substantially the same shape such that the cover and base are not deflected in different or rather opposing directions. More specifically, the distance between a first surface 21 of cover 20 and an opposing first surface 31 of base 30 is substantially uniform. A hardstop tab/ledge associated with the array assay device and/or optional spacers on the backing element, for assisting to maintain the spacing between the backing element and the array assembly at a nominal height, may also be employed, although not shown in these figures.

In certain embodiments as shown in FIGS. 5A and 5B, equal and opposing forces 15, 16' and 16" are employed to achieve this urging (i.e., the deflection) of the cover and base to achieve the same shape and to provide the substantially uniform distance between the cover and the base—thus providing a substantially uniform distance between an array assembly and backing element positioned between the cover and base. Accordingly, the novel urging or deflecting of the cover and base in turn urges or deflects a backing element 22 and array assembly 24 in an analogous manner, i.e., to the same shape and provides a substantially uniform distance between a backing element 22 having at least one gasket 23 and array assembly 24, as shown in FIG. 5B. Specifically, a substantially uniform capillary gap is provided between a first surface 121 of backing element 22 and a first surface 131 of array assembly 24. By bending the backing element and array assembly in substantially the same shape, substantially greater deflection can be tolerated than could be in the configuration of FIG. 3B.

In certain other embodiments as shown in FIGS. 6A and 6B, an array assay device cover 220 (and/or base 230) is configured as a flexure. In use, the flexure cover device deflects a cover and base in substantially the same shape and provides a substantially uniform distance between a backing element 22 having at least one gasket 23 and array assembly 24, as shown in FIG. 6B. The flexure cover serves to assist in providing a reproducible clamping force to an underlying array assembly/backing element structure.

Another way in which a reproducible clamping force may be provided to an underlying array assembly/backing element structure is by employing one or more springs in an array assay device. Accordingly, embodiments include array assay devices that may be spring-loaded such that they may include one or more spring elements or the like for applying a sufficient amount of spring force to a backing element/array substrate structure to provide a sealed assay chamber about an array, i.e., to sufficiently press the structure together, but not provide an amount of force so great as to crush or otherwise damage the backing element/array assembly structure, e.g., break the array substrate and/or break the backing element substrate. The one or more spring elements or the like may be positioned in any suitable area of an array assay device. For example, one or more spring elements may be positioned, e.g., operably integrated, into a cover and/or a base and in certain embodiments a cover and/or base may itself act like a spring element, e.g., a cover (or base) may be a flexure as noted above, which acts like a spring such that a portion of an array assay device may be a flexure body which provides a spring force. Embodiments also include clamping members that act like a spring.

Accordingly, as noted above the subject array assay devices are configured to apply a force to one or both surfaces of a backing element/array substrate structure positioned in the device which results in deflecting the backing element and array assembly into substantially the same shape. In this manner, fluidic contents retained in a gasket element positioned between the backing element and array substrate (i.e., bound by the walls of the gasket and the surfaces of the backing element and array substrate) are prevented from leaking out and/or evaporating from the gasket and a uniform signal may be obtained from the array upon reading the array after an array assay has been performed. Furthermore, the subject array assay devices may be employed to force unwanted gaseous bubbles, within the fluid positioned in a gasket, out of the gasket. This may be accomplished by employing a spring force that pressurizes a bubble. As the backing element and array substrate are clamped together, e.g., using a spring loaded array assay device, the incompressible fluid within the array assay chamber has no where to go and thus pressurized gaseous bubbles are squeezed or forced out through the walls of the gasket. The incompressible liquid, in such instances, serves as a hardstop.

The subject devices are configured to provide a sufficient amount of force to an array assembly/backing element structure, i.e., enough force to operatively clamp the structure together, but not too much force that would damage the structure. More specifically, the force applied to an array assembly/backing element structure held within a subject device may be characterized by the following equation also known as Hooke's Law:

$$F=kx$$

wherein:
"F" is the applied force (SI: N),
"k" is the spring rate or constant (SI: N/m), and
"x" is the displacement from equilibrium position (SI: m).

As "x" is fixed in the subject invention, e.g., by limiting the number of turns of a screw or the like, the subject invention provides novel array assay devices that control or provide an appropriate, reproducible spring rate "k". For example, embodiments include dictating or defining the spring rate by one or more of: spring elements in an array assay cover, a flexure of a clamping member, i.e., a clamping member flexure, and flexure in an array assay cover, i.e., an array assay flexure cover.

In certain embodiments, the spring rate may not be uniform, which may help keep the force uniform with variations in "x". For example, a F,x curve for a Belleville washer (also known as a disk spring) may appear as illustrated in FIG. 10 showing a plot of force vs. spring deflection ("x") for a typical, linear spring 650 and for a non linear spring (for example a Belleville washer or the like) 600.

Common to all of the subject array assay devices is a base member, a mateable cover member and a clamping member, e.g., a flexure clamping member, where the cover and the base are dimensioned to retain a backing element/array assembly structure therebetween. In all of the subject array assay devices, when the base and the cover are joined together in a closed configuration by actuation of the clamping member, e.g., a clamping member may be screw-operated or the like, an appropriate, e.g., optimal, amount of force is provided to the backing element and an array assembly, resulting in a sufficient amount of force to compress them together to the nominal distance between the backing element and array assembly, but not so much force as to damage the backing element and array assembly or any of the array assay components.

The array devices of the subject invention may assume a variety of shapes ranging from simple to complex, with the only limitation being that they are suitably shaped to receive and retain at least one array substrate having at least one array present on a surface thereof. The array assay devices are usually ergonomically designed for ease—of use and handling. It will be apparent that the shapes of the base and the cover may differ or may be the same. In many embodiments, the array assay devices will assume a circular, oval, oblong, square or rectangular shape, although other shapes are possible as well, such as irregular or complex shapes. For example, in those embodiments where a substrate, e.g., a 1"×3" glass microscope slide as is known in the art, includes one or more arrays, the array assay device may have an analogous rectangular shape.

The size of the array assay devices may vary depending on a variety of factors, including, but not limited to, the size of the array substrate and the like, where the sizes of the base and the cover may differ or may be the same. Generally, the array assay devices are sized to be lightweight and easily transportable or moveable. In certain embodiments of the subject devices that have a substantially rectangular shape, the length of the array assay device may range from about 10 mm to about 200 mm, e.g., from about 20 mm to about 100 mm, e.g., from about 50 mm to about 100 mm, the width may range from about 10 mm to about 100 mm, e.g., from about 20 mm to about 50 mm, e.g., from about 40 mm to about 50 mm and the thickness may range from about 2 mm to about 100 mm, e.g., from about 4 mm to about 50 mm, e.g., from about 15 mm to about 35 mm. However, these dimensions are exemplary only and may vary.

Accordingly, the subject array assay devices are dimensioned such that a backing element/array assembly structure with at least one gasket therebetween may fit or be operatively positioned in the devices. In other words, a subject array assay device has dimensions (length, width and thickness) which enable a backing element and an array substrate having at least one array (i.e., a backing element/array assembly structure) to be retained between the base and cover of the device when the device is in a closed configuration, i.e., the backing element and array substrate would be completely enclosed by the closed array assay device. For example, in certain embodiments, the backing element/array assembly structure may have a combined (i.e., total) length that ranges from about 60 mm to about 80 mm, usually from about 70 mm to about 80 mm and more usually from about 74 mm to about 78 mm, a combined width that typically ranges from about 20 mm to about 40 mm, usually from about 24 mm to about 30 mm and more usually from about 25 mm to about 30 mm and a combined thickness that typically ranges from about 0.9 mm to about 4 mm, usually from about 1 mm to about 3.5 mm and more usually from about 1 mm to about 2 mm, where an array assay device used with such a backing element/array assembly structure would have the dimensions as described above.

The subject array assay devices may be fabricated from a wide variety of materials. Specifically, the materials should be chemically and physically stable under conditions employed for the array assay. The material(s) used to fabricate the base may differ from the material(s) used to fabricate the cover or may be the same. Usually, though not always, one or both of the base and/or the cover are rigid or portions thereof are rigid. By rigid it is meant that the base and cover cannot be substantially bent or folded without breaking with the force normally employed in using an array assay to perform an array assay protocol. Such rigidity enables the device to apply and withstand compression forces applied thereto and/or thereby. Examples of materials which may be used to fabricate the array assay devices include, but are not limited to, plastics such as polytetrafluoroethylene, polypropylene, polystyrene, polycarbonate, PVC, and blends thereof or that include fillers for added stiffness and strength, ceramics, stainless steel, alloys thereof and other corrosion-resistant alloys and, siliceous materials, e.g., glasses, fused silica, and the like. The subject devices or any component thereof may be manufactured to be re-useable or single use. That is, one or more components of the subject array assay devices may be reusable while other components may be single use. For example, a base and a cover may be manufactured to be re-useable, while the backing element may be manufactured to be single-use or disposable, or vice versa.

Exemplary array assay devices are now described in greater detail in turn. In describing the operation of the subject array assay devices, the array assay devices are described primarily as having a backing element with at least one gasket positioned in the base of the housing, followed by the contact with an array substrate having one or more arrays, where this description is for exemplary purposes only and is in no way intended to limit the scope of the invention. It will be apparent that the array substrate may-be first positioned in the base and a backing element having at least one gasket may then be contacted thereto. Still further, it will be understood that a gasket may be permanently affixed to a backing element substrate or may be readily separable therefrom.

Figure 7B:
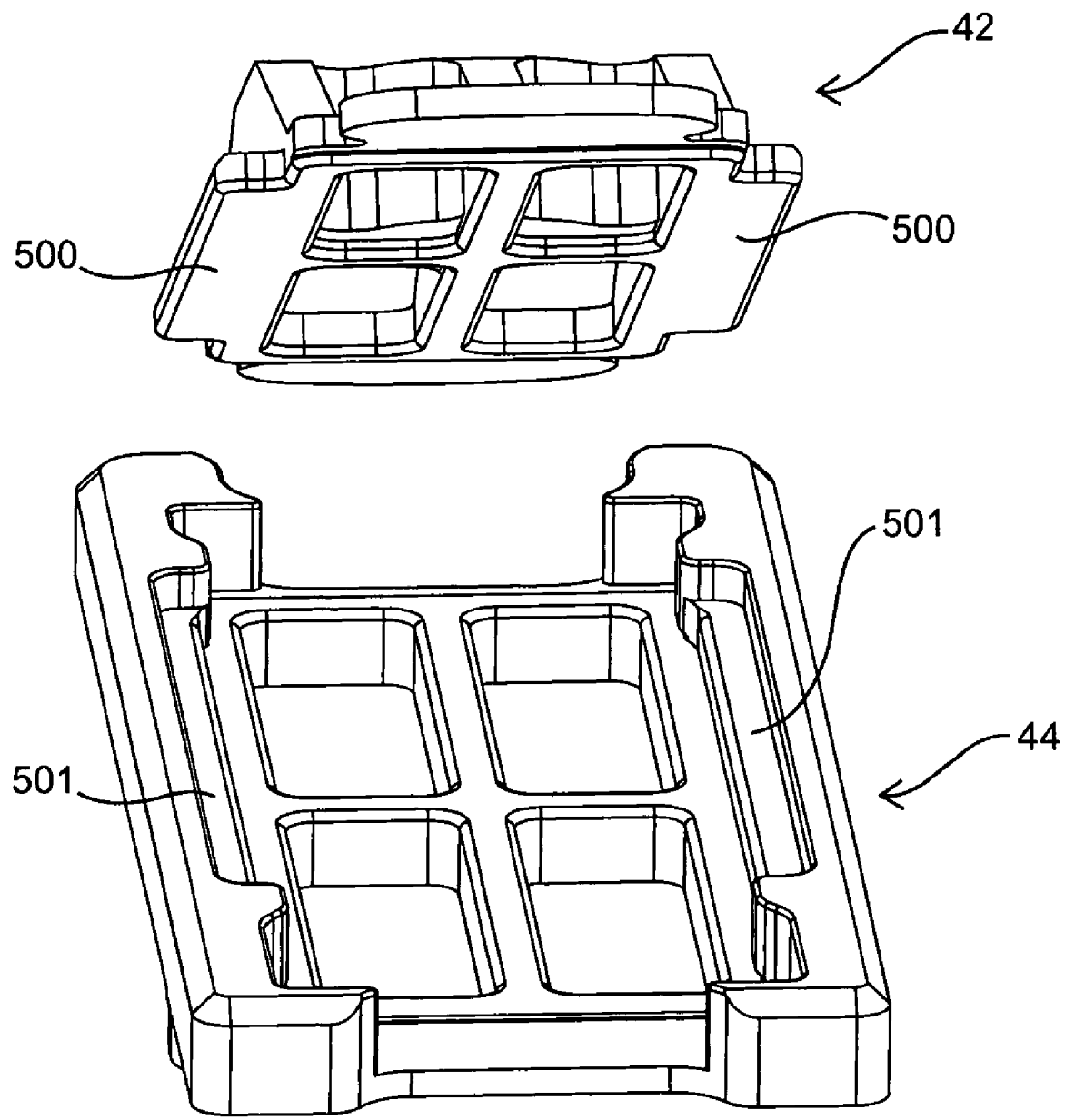
Figure 7C:
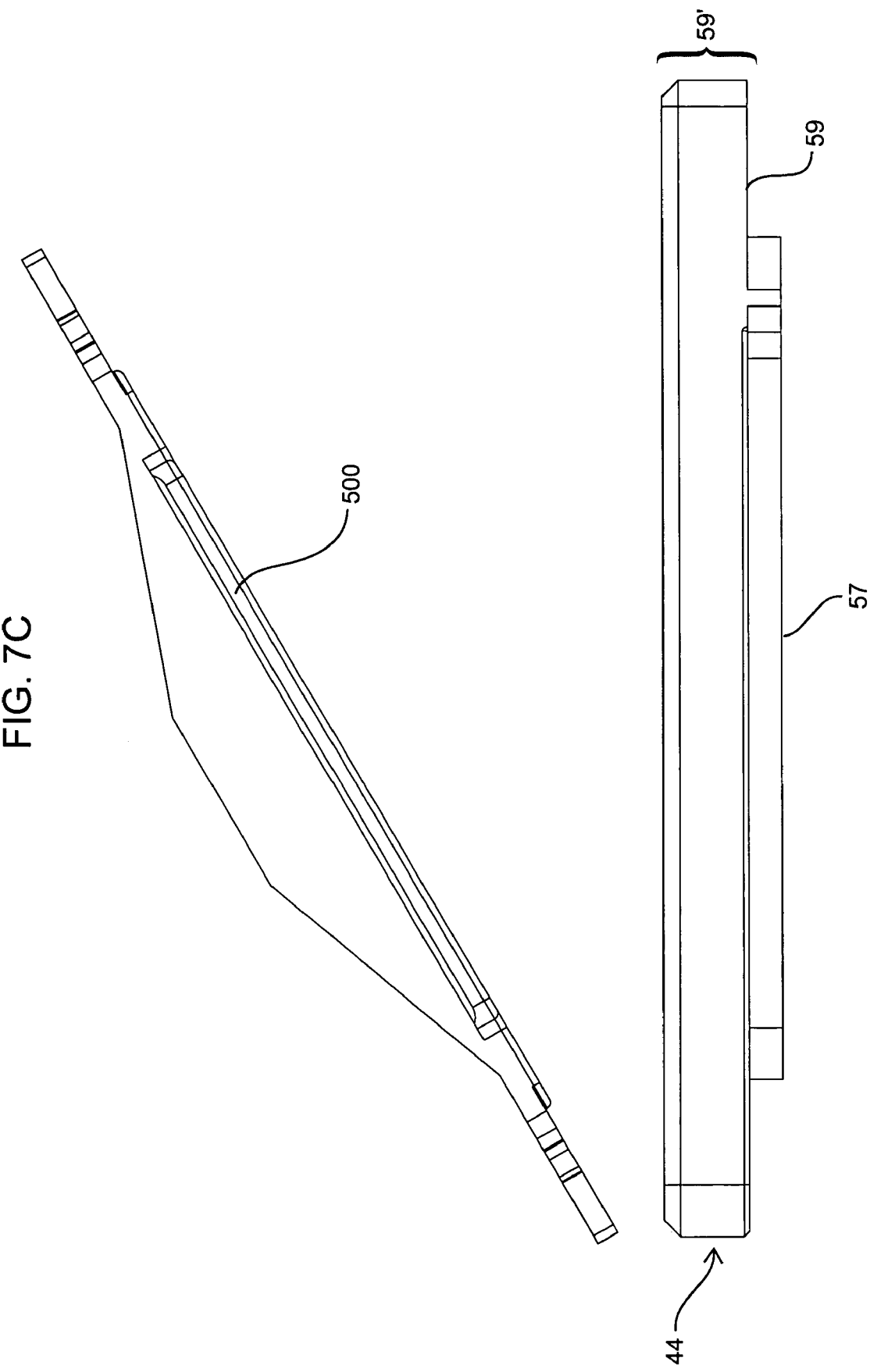
Figure 7D:
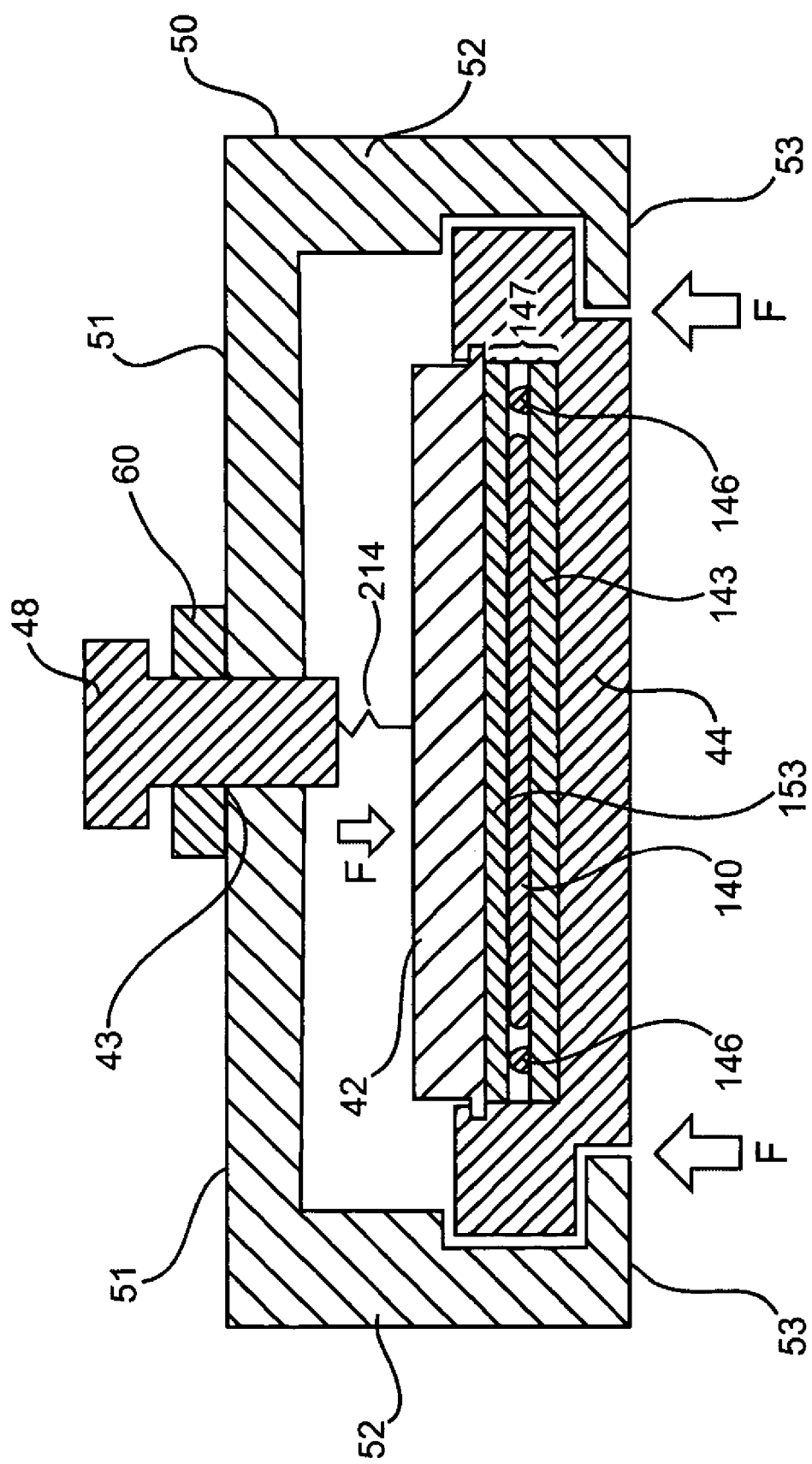
Figure 7F:
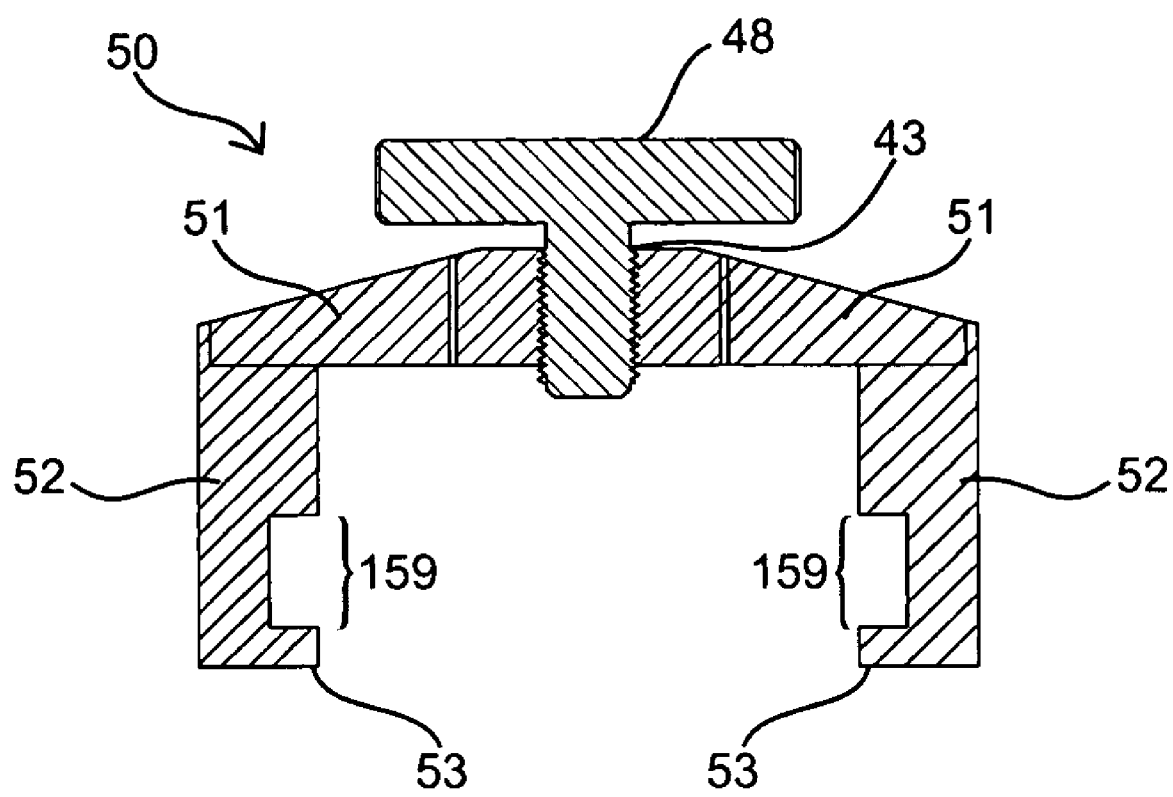

FIGS. 7A-7F show an exemplary embodiment of an array assay device. FIGS. 7A, 7D (cross sectional view) and 7E (side view) show an exemplary embodiment of such a device in a fully assembled configuration, i.e., with the array assay device cover held together to the array assay device base using a clamping member; FIGS. 7B and 7C (side view) show the cover and base in an open position and FIG. 7F shows an exemplary embodiment of a clamping member (e.g., a flexure clamping member) that may be employed with the cover and base. As described in greater detail below, embodiments of the clamping member provide equal and opposing forces to two surfaces (i.e., the top and the bottom) of a backing element/array assembly structure and deflects the backing element and array assembly in substantially the same shape when clamped down using a screw or other analogous method.

As shown in FIG. 7A, device 40 includes a cover 42, a mateable base 44 and a clamping member 50 that is configured to slide over cover 42 and base 44 when they are contacted together. Clamping member 50 (as well as clamping members of other embodiments) may or may not be a flexure clamping member. In other words, clamping members of the subject invention may be configured as, and act like, a flexure such that the spring effect may be achieved by the clamping member acting like a flexure. As shown is FIG. 7D which is a schematically illustrated cross-sectional view taken along lines C-C of FIG. 7A, a knob or screw 48 of clamping member 50 may be actuated to provide forces, i.e., equal and opposing forces ("F"), to a structure, herein represented by structure 147 of FIG. 2A-2C, positioned between the cover and the base, i.e., to the backing element/array assembly or rather to the gasket element(s) positioned therebetween. In so doing, the backing element and array assembly are deflected in substantially the same shape. Also as shown in FIG. 7D, optional spacers 146 are positioned between the array assembly and the backing element. One or more optional spring elements 214 may also be provided. A spring element, if included, may be any suitable spring element as described in greater detail below, i.e., may be a Belleville disk spring, helical disk spring, leaf spring, and the like, or a combination thereof.

Accordingly, such devices include a clamping member 50 that includes a turnable or rotatable knob or screw 48 threadably disposed within bore 43 of the flexure bridge (see for example FIGS. 7D and 7F). Clamping member 50 includes shoulders 51 and extending arm portions 52 that terminate at feet 53 which when operatively positioned with a base are positioned on the underside 57 of the base. As such, feet 53 are configured to be positioned adjacent a bottom surface 59 (see for example FIG. 7C) of the base such that tightening of the screw and thus clamping together base and cover provides a reaction force to the base via feet 53 if a spring action from the clamp is desired. Shoulders 51 may be designed with a geometry to allow a flex upon actuation of screw 48, and as such the clamping member may be characterized as a flexure clamping member because it is configured as a flexure. Accordingly, a spring force may be provided by the flexure clamping member as screw 48 is actuated to clamp the cover and base together. As such, the flexure clamping member devices may be characterized as spring loaded devices. Certain embodiments may include a spring element, as shown in FIG. 8 and as described below.

As shown in the open configuration of the cover and base shown for example in FIGS. 7B and 7C, hardstop elements are provided. More specifically, cover 42 includes hardstop tabs 500 which are dimensioned to fit with and be positioned upon corresponding hardstop ledges 501 of base 44. As noted above, instead of or in addition to hardstop tabs/ledges, spacers may be provided positioned between the backing element and array assembly. By hardstop, bumper or spacer is meant broadly to include any physical component, material, interface, process or configuration that limits the travel of at least one of an array assay device base and an array assay device cover as they are forced or clamped (i.e., operatively held together) with a clamping member (thus controlling the capillary height between an array assembly/array backing element structure positioned therebetween). Accordingly, embodiments of the subject invention may include one or more hardstops (which typically include a tab on a cover and/or base and corresponding ledge on a cover and a base for positioning the tab and which tab/ledge hardstop configuration may be collectively be referred to as a hardstop) or spacers which may be positioned on at least one of: a backing element, array assembly, array assay device base and array assay cover. The hardstops and spacers may be integral with an array assay device, array assay chamber, or component(s) thereof, i.e., fixedly attached or may be a separable component that is not fixedly attached to any specific component. Regardless of how a hardstop and/or spacer is provided, in such embodiments the subject array assay devices, in which the cover and base are urged in substantially the same direction, force contact along the entire lengths of the hardstop (and/or spacer) thereby improving uniformity of the capillary gap between the array assembly and backing element. Exemplary hardstop/spacer configurations that may be employed in the subject invention are described for example in U.S. patent application Ser. No. 10/283,450, the disclosure of which is herein incorporated by reference.

FIG. 7F provides a cross sectional view of clamping member 50, e.g., as taken through line C-C of FIG. 7A. As shown, feet 53 of clamping member 50 are provided by cut-outs or slots 159 of laterally extending portions 52. The slots are dimensions to be commensurate with a thickness of at least a portion of a base member to which it is to be engaged such as thickness 59' of FIG. 7C so as to slide over and operatively engage the base.

Accordingly, device 40 is configured to apply a force to a backing element and an array assembly, having at least one gasket positioned therebetween, when present in the device by clamping the backing element and array assembly together using the clamping member which may be actuated or clamped down using any appropriate method, e.g., by actuating knob or screw 48. When the backing element and array substrate are pressed together by the cover and the base by tightening the screw, the two are deflected into substantially the same shape.

A backing element used with a subject array assay device may be a separate component or may be integrally formed or molded with the base as a single piece. In operation, a first substrate such as a backing element is positioned in the base with the one or more gaskets facing the cover or forward, i.e., facing out of the page. In certain embodiments, a second substrate such as an array assembly is held on the interior or underside of the cover by brackets or the like (not shown), such that when the cover is associated with the base to form a closed device, the array is contacted with the backing element supported sample. Alternatively, the second substrate, e.g., an array assembly, may be contacted with the backing element supported sample by manually placing (independent of the cover) the second substrate onto the first substrate before engaging the base and the cover together. Specifically, in use a first substrate, e.g., a backing element, may be positioned in base 44 with the one or more gaskets facing out of the page. A sample may be contacted with the interiors of the gasket(s) to provide a backing element supported sample. Next, a second substrate having at least one array may be contacted with the backing element supported sample such that an enclosed assay area around each array may be provided, at which point cover 42 may be associated with base 44 in a closed configuration. As mentioned above, contacting the array with the backing element supported sample and associating the cover with the base may be accomplished simultaneously. At this point, clamping member 50 may be slideably moved over the closed array assay device structure (having the backing element/array assembly structure therein) and screw 48 is turned to advance or thread the screw through bore 43 to contact cover 42 (or optional spring element(s) of a cover). As too many turns of the screw may damage the array assembly/backing element structure, a user may be instructed to turn the screw a certain number of times and/or the device may include physical means to stop the screw from being turned passed a certain point or rather from being turned too much or may include a screw with a suitable threading configuration commensurate with, for example a certain, optimal number of turns. For example, a screw stop member such as optional screw stop 60 shown in FIG. 7D may be provided that physically prevents the screw from being turned passed a certain point or more than a certain number of turns. In any event, means may be provided that ensures a repeatable, force is applied to the backing element/array assembly structure. In any event, the array assay device presses the array assembly and backing element together to urge the two together in substantially the same direction all along the length of the contacting surfaces thereof to provide a substantially vapor and fluid tight seal or assay area around the one or more arrays on the array substrate. As noted above, such may also force any unwanted gaseous bubbles present in fluid contained within a gasket, through the gasket walls and into the exterior environment.

Spring Elements

As noted above, embodiments may include array assay devices that include one or more spring elements and specifically a cover that includes one or more spring elements. Accordingly, certain embodiments of the subject invention include a spring element that may be compressed by a screw or other analogous structure to apply a spring force to a backing element/array assembly structure. FIG. 8 shows an exemplary embodiment of disk spring array assay device cover. Embodiments of the disk spring array assay cover may be analogous to the above-described cover in that a clamping member (not shown) such as a clamping member (flexure or not) and knob or screw or other analogous structure is employed to apply a compression force to the cover and base of the device, which, in turn, applies a force to the underlying structure, i.e., to the backing element/array assembly structure, present in the device to deflect them to substantially the same shape. The one or more spring elements are operatively positioned in the cover in this embodiment, i.e., the spring element is a separable component from the cover, but is positioned in the cover. A spring element may also be positioned in a base instead of or in addition to the cover. Advantageously, an additional benefit of employing a spring-controlled force that the individual components of an array assay device may be made thinner and lighter and thus less expensive, than conventional array assay devices.

Specifically, in accordance with this embodiment, one or more spring elements are operatively positioned in the cover of an array assay device. Accordingly, a spring force from the one or more spring elements facilitates that a reproducible force is applied to the backing element/array assembly structure via the clamping member because the amount of force that a user can apply to the assembly is limited. Typically, the disk spring element(s), as shown, provide a non-linear ratio of deflection to load. In this manner, if the screw or other analogous component is turned too much, the backing element/array substrate structure will not be damaged.

FIG. 8 shows an exploded view of a disk spring cover 68 that includes a retaining ring 61, button 62 and one or more spring elements 63 (shown here as one spring element). The cover includes a bore or hole 64 or analogous depression that is configured to accommodate the retaining ring, button and one or more spring elements, e.g., hole 64 may be a flat bottom hole with a groove 66 for accommodating the retaining ring.

Any suitable spring element(s) may be employed where, as noted above, usually the amount of deflection provided by the spring element is non-linearly related to the load applied to it. For example, in many embodiments the maximum deflection of a given disk spring employed in the subject invention ranges from about 0.05 mm to about 20 mm, e.g., from about 0.1 mm to about 20 mm, e.g., from about 0.2 mm to about 20 mm, e.g., 3 mm to about 10 mm. The outer diameter of a spring may range from about 2 mm to about 100 mm, e.g., from about 5 mm to about 25 mm, e.g., from about 5 mm to about 15 mm; the inner diameter may range from about 1 mm to about 75 mm, e.g., from about 2 mm to about 15 mm, e.g., from about 3 mm to about 10 mm; the thickness may range from about 0.02 mm to about 5 mm, e.g., from about 0.05 mm to about 2 mm, e.g., from about 0.1 mm to about 0.8 mm. Suitable spring elements include disks springs such as Belleville disk springs, helical disk springs, leaf springs, and the like.

The number of spring elements that may be employed may vary, where the number may range from about 1 to about 55, e.g., from about 1 to about 20, e.g., from about 1 to about 10. In embodiments having a plurality of spring elements, typically the spring elements will be stacked together, i.e., positioned one on top of the other, but could be in multiple stacks of one or more side by side.

Accordingly, spring element 63 is configured to apply a spring force to a backing element/array assembly structure when present in the disk spring cover array assay device by actuating knob or screw 48. Analogous to that described above, in use the array assay device presses the array assembly and backing element together to urge the two together in substantially the same direction all along the length of the contacting surfaces thereof to provide a distance between the backing element and array substrate that is substantially uniform and a substantially vapor and fluid tight seal or assay area around the one or more arrays on the array substrate.

Flexure

As noted above, embodiments may include array assay devices that include a flexure array assay device. The flexure may be integral to an array assay device or may be a separate piece or more than one separate pieces. Accordingly, certain embodiments of the subject invention may include a flexure cover and/or flexure base and/or flexure clamping member such that the flexure cover and/or flexure base and/or flexure clamping member performs like a spring and applies a spring force to an array assembly/backing element structure. The subject flexure devices are further primarily describe with respect to a flexure cover for convenience only, where such description is in no way intended to limit the scope of the invention as it is to be understood that one or more flexures may be in the cover and/or base and/or clamp and/or in any other component.

Embodiments of flexure array assay devices in accordance with the subject invention include a flexure body that provides a spring force, instead of or in addition to a separable spring element for such a purpose as described above in regards to the disk spring array assay devices. Thus, the cover of a flexure cover array assay device is one part or a single component. FIGS. 9A-9F show an exemplary embodiment of a flexure cover 70 for use with a Flexure Cover array assay device having a first side 70*a* and a second array assembly contacting side 70*b*. Flexure cover 70 includes a screw contact area 71 where a screw or another analogous component will press on the flexure cover. A feature of the flexure covers is the presence of slots 73 integrally formed within the cover. The slots are dimensioned and positioned to achieve a flexure, i.e., to provide suitable flexing of the cover in response to actuation of a screw. More specifically, as a screw is tightened to press against the flexure cover, the region of the flexure cover above the slots provides a beam which acts like, e.g., a leaf spring. In other words, the cover itself acts like a leaf spring. Accordingly, a spring force is applied by the cover to an array assembly/backing element structure positioned between the cover and a base. Bridges 72 are dimensioned to prevent over-deflecting to a point of yield stress, i.e., to limit the flexure travel. In this flexure cover embodiment, flexing is achieved in the region generally marked by dashed lines 76 in FIG. 9B. Flexure cover 70 may also include hardstop tabs 77 which are dimensioned to fit or align with corresponding hardstop ledges on a base to be used with the cover. The force applied to an array assembly/backing element structure positioned between the cover and a base deflects the structure in a uniform or rather the same shape and provides a substantially uniform distance between the array assembly and backing element.

Figure 9C:
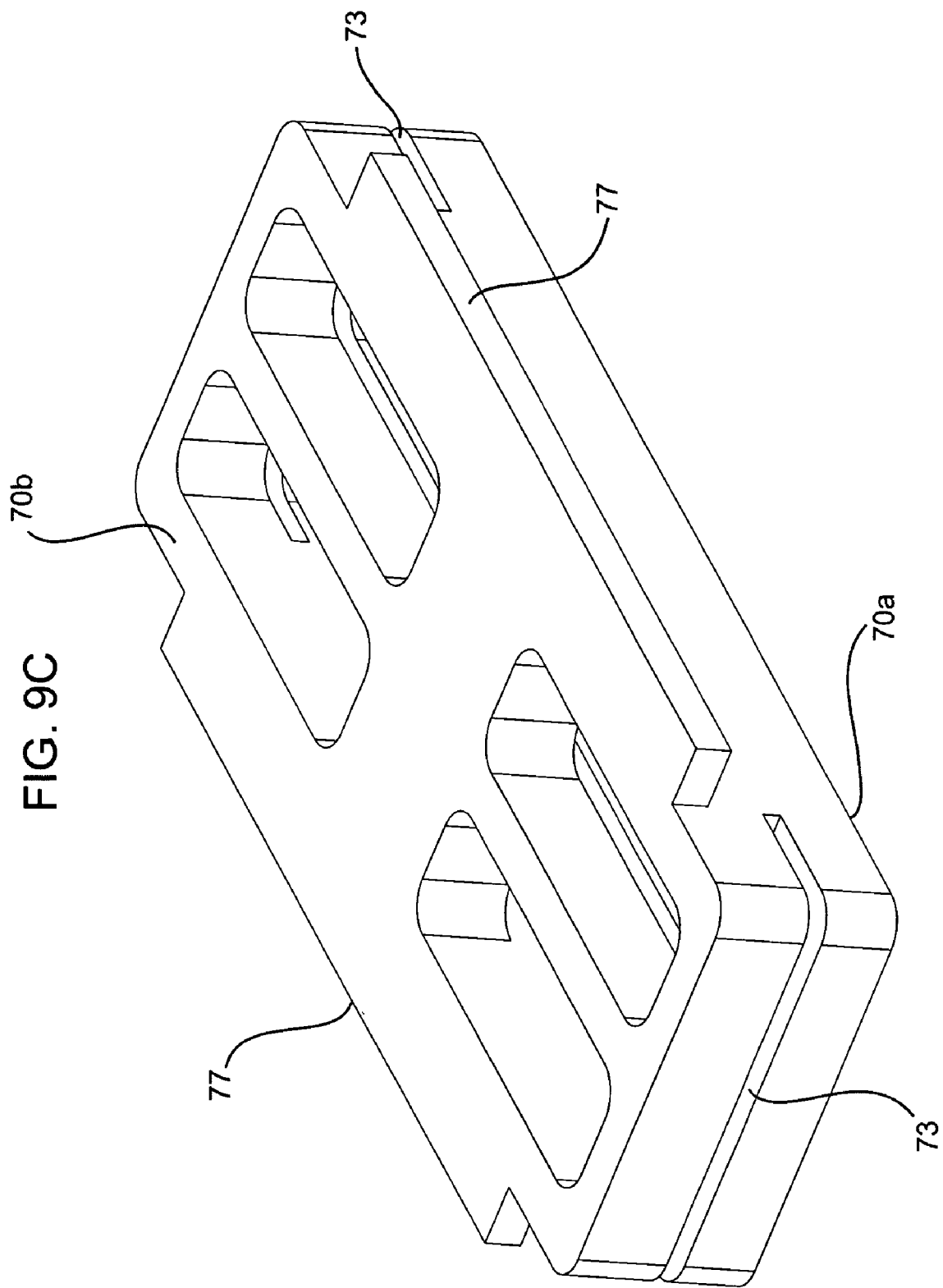
Figure 9D:
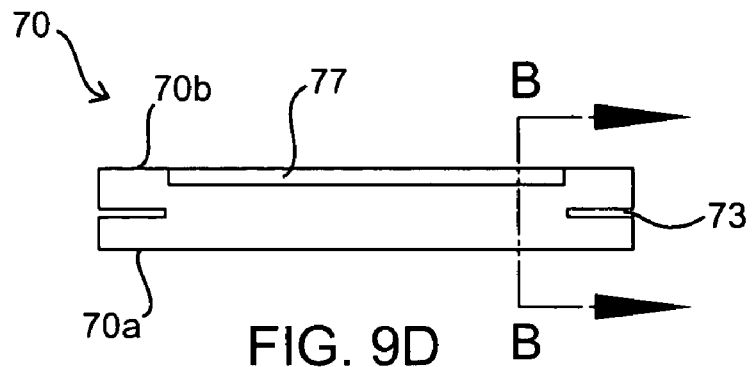
Figure 9E:
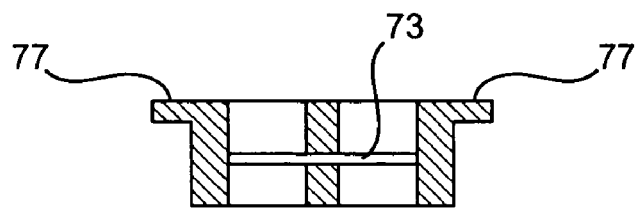
Figure 9F:
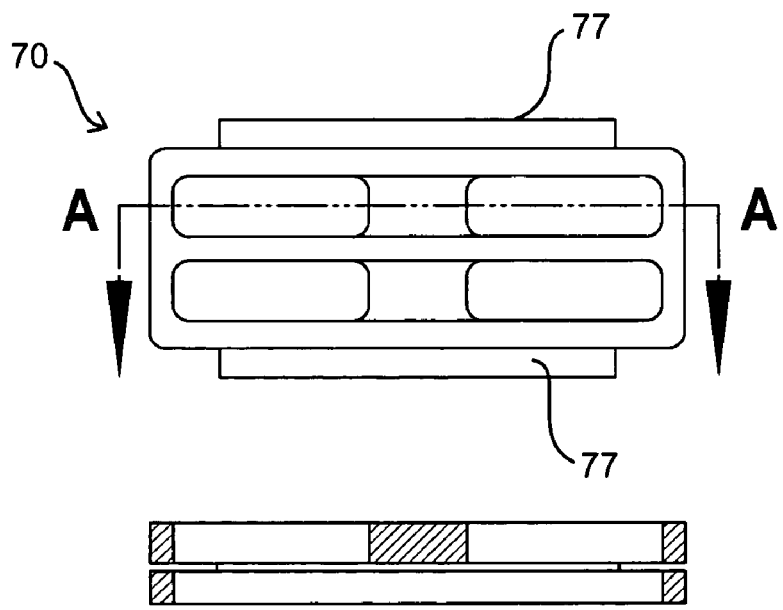
Figure 9G:
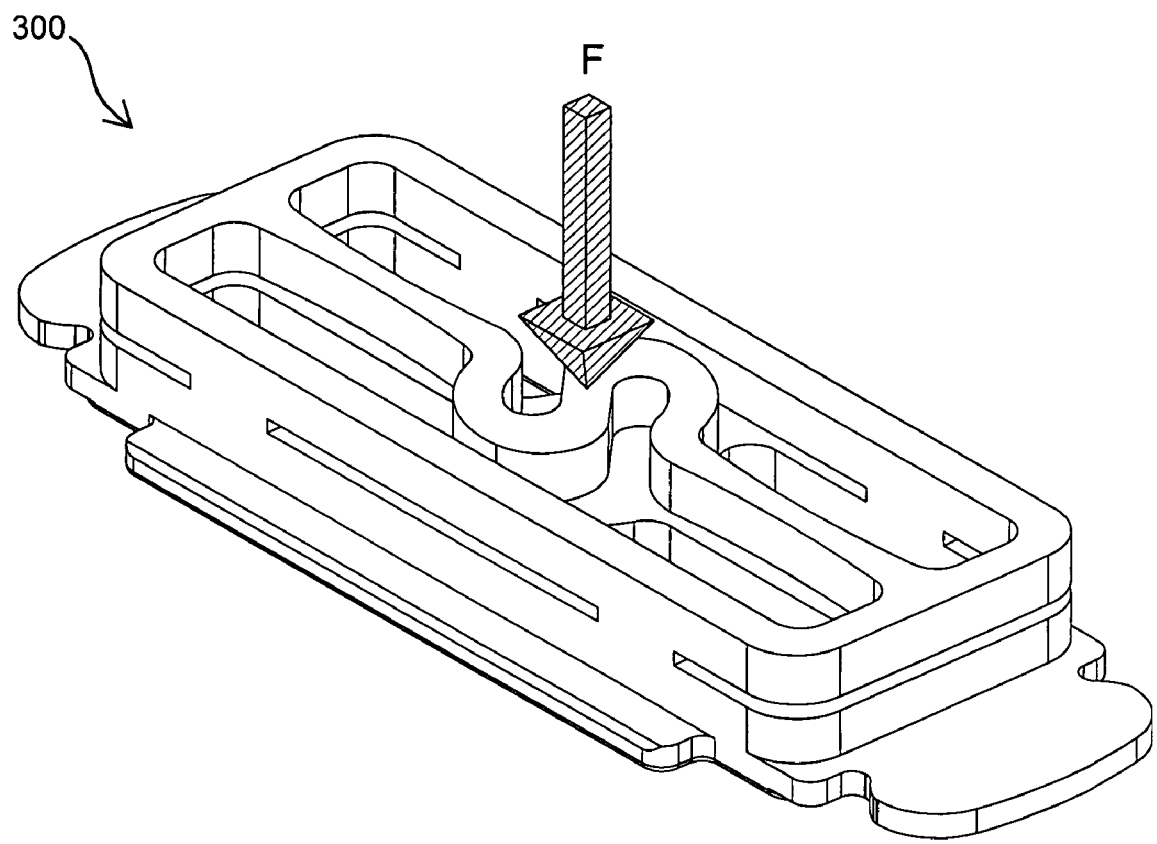

FIGS. 9D-9F show various other views of flexure cover 70 wherein FIG. 9D shows a side view of flexure cover 70, FIG. 9E shows a cross-section view taken along line B-B of FIG. 9D, and FIG. 9F shows a top view of flexure cover 70 and FIG. 9F shows a cross-section view taken along line A-A of FIG. 9F.

FIG. 9G shows another exemplary embodiment of a flexure cover 300 which also includes slots integrally formed within the cover, analogous to that described above. The slots are dimensioned and positioned to achieve a flexure, i.e., to provide suitable flexing of the cover in response to actuation of a screw that provides a force F to the cover.

The use of a flexure cover array assay device is analogous to that described above. That is, in operation a first substrate such as a backing element is positioned in an array assay base with the one or more gaskets facing the cover or forward, i.e., facing out of the page. In certain embodiments, a second substrate such as an array assembly is held on the interior or underside of the cover by brackets of the like (not shown), such that when the cover is associated with the base to form a closed device, the array is contacted with the container element supported sample. Alternatively, the second substrate, e.g., an array substrate, may be contacted with the backing element supported sample by manually placing (independent of the cover) the second substrate onto the first substrate before engaging the base and the cover together. Specifically, in use a first substrate, e.g., a backing element, may be positioned in a base with the one or more gaskets facing out of the page. A sample may then be contacted with the interiors of the gasket(s) to provide a backing element supported sample.

Next, a second substrate having at least one array may be contacted with the backing element supported sample such that an enclosed assay area around each array may be provided, at which point an array assay flexure cover may be operatively associated with the base in a closed configuration, e.g., hardstop tabs of the flexure cover may be aligned or positioned adjacent corresponding hardstop ledges of the base. As mentioned above, contacting the array with the substrate supported sample and associating the flexure cover with the base may be accomplished simultaneously. At this point, a clamping member may be slid over the closed device and clamped down by turning a screw to advance or thread the screw through a bore of the clamping member to press the screw against the surface of the flexure cover to flex the cover in a suitable manner, e.g., to provide flexing along the area marked by dashed lines 76 in FIG. 9B. In so doing, the regions above the formed slots 73 create a beam which serves as a spring that provides a force to an array assembly/backing element structure positioned between the flexure cover and base. The force provided from the flexure presses the array substrate and backing element together to deflect them in substantially the same direction and to provide a substantially vapor and fluid tight seal or assay area around the one or more arrays on the array substrate.

Systems

Also provided by the subject invention are systems that include the subject array assay devices. The subject systems include an array assay device cover, an mateable array assay base and a clamping member for holding the cover to the base about a backing element/array assembly structure, as described above. For example, the systems may include a subject array assay device, which may include a disk spring cover, flexure cover, flexure clamping member, etc. The subject systems may also include suitable apparatuses for performing an array assay using a subject cover, base and clamping member. For example, certain system embodiments may include an incubator for maintaining the assay components at a suitable temperature during some or all of an array assay protocol or other array assay stations, e.g., automated hybridizations station.

The subject systems may also include an array assembly, i.e., an array substrate having at least one array. Backing elements may also be included in the subject systems. In certain embodiments, the subject systems may further include reagents employed in array based assay protocols, including sample preparation reagents, e.g., labeling reagents, etc; washing fluids; etc.

Methods

As summarized above, methods are provided for performing an array-based assay such as a hybridization assay or any other analogous binding interaction assay. In practicing embodiments of the subject methods, a sample suspected of including an analyte of interest, e.g., a target molecule, may first be contacted with a first surface of a first substrate, e.g., a first surface of a backing element or an array substrate, to produce a substrate supported sample, e.g., a backing element-supported sample, where the first surface includes at least one area bounded on all sides by a gasket element which retains the sample. Once a backing element supported sample is provided, a second substrate such as an array assembly may be contacted with the backing element supported sample to provide a structure that includes the first and second substrates with a gasket element positioned therebetween. The structure may then be held together using a subject array assay device such that in use, the structure is bend or deflected in a single direction, i.e., both components of the structure are urged in the same direction thus providing a uniform capillary gap therebetween, i.e., the distance between the two substrates is substantially uniform.

Accordingly, embodiments of the subject methods may include an initial step in which a substrate supported sample, e.g., backing element supported, is produced from an initial sample, where the substrate supported sample may then be contacted with a second substrate such as an array substrate. The substrates may then be maintained a substantially uniform distance apart and a seal or barrier is provided around the array formed by the walls of a gasket and the surfaces of the backing element and array substrate.

Accordingly, the resultant backing element supported sample may be contacted with an array assembly and a force may then be applied to the first and second substrates (i.e., to the backing element and the array) to compress them together, i.e., the two substrates may be clamped together. A suitable clamping force may be provided by at least one of disk springs, flexure cover and flexure clamping member. In this manner, the sample may be effectively retained within the container element(s) to prevent sample leakage and/or evaporation from the assay area and all parts of the array will be contacted by sample present within the array assay chamber with uniformly distributed reactants, i.e., all parts of the array will be bathed in the same concentrations of reactants during the array assay. Furthermore, unwanted gaseous bubbles in the sample may be forced out of the assay area via diffusion through the gasket walls.

Accordingly, embodiments of the subject methods include contacting a sample, or other fluid such as wash buffer, etc., with a first surface of a first substrate, i.e., a first surface of a backing element. A feature of the first surface of the first substrate is that at least an area thereof it is bounded on all sides by a gasket. As noted above, the gasket may be an integrally formed gasket with respect to the first substrate, or may be a separate component that is otherwise adhered to the first substrate. Still further, the gasket may be a removable or readily separable gasket. The gasket may be positioned on the backing element or on the array substrate, whichever is convenient for a given protocol, but in many embodiments is positioned on the backing element. In further describing the subject methods, reference to a backing element having a gasket will be primarily used to describe the invention, where such description is exemplary only and is in no way intended to limit the scope of the invention.

In practicing embodiments of the subject methods, a quantity of a fluid sample to be assayed may be first contacted with the first surface of a first substrate, further described with reference to a first surface of a backing element, to produce a backing element support sample. That is, the sample may be introduced into the gasket element present on the first surface of a first substrate, e.g., a backing element, so that the sample is retained thereby. In those embodiments having more than one gasket element, the same sample may be applied to one or more gasket elements, for example when it is desirable to test the same sample with different arrays during the same assay procedure, or a different sample may be applied to one or more gaskets than is applied to one or more other gaskets, for example when it is desirable to test different samples with the same array or different arrays during the same array assay procedure. In any event, a sample may be introduced into a gasket element using any convenient protocol, where in many embodiments a deposition type protocol is employed, e.g., by pipette or the like. A needle is not required to apply the sample to the container element because the gasket is easily accessible at its opened top end at this step in the subject methods.

Once the sample has been contacted with the backing element and the sample is contained by the gasket element, the resultant backing element supported sample, e.g., backing element or container supported sample, may then be placed in contact with a second substrate (an array of binding agents that include a binding agent specific for the analyte of interest) such that the gasket element is disposed between the backing element substrate and array assembly such that the array side of the array substrate faces the backing element, i.e., the at least one array is bounded by the at least one gasket.

At any point, the backing element and array substrate may be operatively positioned in a subject array assay device. For example, the backing element may be positioned in a subject array assay device or rather positioned in the base of an array assay device (e.g., the backing element may be provided to the user already in an array assay device, for example integrally formed therein, etc.), a sample applied to the backing element positioned in the array assay device and then the array assembly may be positioned thereover. In another example, the backing element may be initially outside a subject array assay device, sample contacted thereto, the second substrate positioned thereover and the resultant backing element supported sample then positioned in a subject array assay device. In any case, the sample may be contacted with an array, at which point the cover of the array assay device may be closed or rather brought in contact with the base such that the cover and base are in a closed configuration about the backing element/array assembly structure.

Once the cover is contacted with the base about the backing element/array assembly structure, the clamping member may be slid over the closed array assay device and a screw or other analogous component may be tightened which results in a compression force applied to the backing element/array assembly structure such that the backing element and array substrate are pressed together and urged in substantially the same direction and a substantially uniform distance is provided between the backing element and array assembly. In this manner, the sample is retained in contact with the entire area of the array.

The sample is contacted with the one or more arrays under conditions sufficient for any target analyte present in the sample to bind to its respective binding pair member that is present on the array. Thus, if the analyte of interest is present in the sample, it binds to the array at the site of its complementary binding member and a complex is formed on the array surface. As noted above in the review of representative arrays, a number of different types of arrays may be employed.

As described above, a feature of the subject methods is that, once the substrate supported sample is contacted with a second substrate, a force is applied to the resultant structure, i.e., the substrate carrying the one or more arrays and the backing element, to compress or press the backing element and the substrate of the array together and deflect them in substantially the same direction with the gasket retained sample therebetween. As such, the application of this compression force ensures that the array and backing element remain positioned relative to each other in such a way as to provide a substantially uniform distance therebetween and a tight seal or barrier around the array defined by the walls of the fluid barrier of the gasket, the first surface of the backing element and the array substrate. The compression force is applied uniformly to the backing element/array structure and thus uniformly to the gasket therebetween so as to prevent leakage and/or evaporation of the sample from the enclosed area. This compression force may be applied using any subject array assay.

While maintaining the backing element and array in a compressed state, the resultant compressed sample contacted array structure is then maintained under conditions sufficient, and for a sufficient period of time, for any binding complexes between members of specific binding pairs to occur. Where desired, the sample may be agitated to ensure contact of the sample with the array. In certain embodiments, mixing may be accomplished by providing a bubble of air in the enclosed assay chamber, i.e., with the sample, where the movement of the bubble during the array assay assists in mixing or moving the sample. In the case of hybridization assays, the substrate supported sample may be contacted with the array under stringent hybridization conditions, whereby complexes are formed between target nucleic acids that are complementary to probe sequences attached to the array surface, i.e., duplex nucleic acids are formed on the surface of the substrate by the interaction of the probe nucleic acid and its complement target nucleic acid present in the sample. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate. Hybridization involving nucleic acids generally takes from about 30 minutes to about 24 hours, and may vary as required. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

Once the incubation step is complete, the one or more arrays may be washed at least one time to remove any unbound and non-specifically bound sample from the substrate, generally at least two wash cycles are used. To do this, the screw is loosened to relieve the force applied to the backing element/array substrate structure. The cover may then be removed to provide access to the array. The array may then be separated from the backing and contacted with one or more washing agents, where the array may be washed while positioned in the array assay device or may be removed from the array assay device to be washed. Washing agents used in array assays are known in the art and, of course, may vary depending on the particular binding pair used in the particular assay. For example, in those embodiments employing nucleic acid hybridization, washing agents of interest include, but are not limited to, solutions such as salts solution, e.g., sodium phosphate and sodium chloride, and the like as is known in the art, at different concentrations and may include some surfactant as well.

Following the washing procedure, as described above, the array may then be interrogated or read so that the presence of any resultant binding complexes on the array surface may be detected, e.g., through use of a signal production system, e.g., an isotopic or fluorescent label present on the analyte, etc. The presence of the analyte in the sample may then be deduced from the detection of binding complexes on the substrate surface.

For example, reading of the array may be accomplished by illuminating the array and reading the location and intensity of resulting fluorescence at each feature of the array to detect any binding complexes on the surface of the array. For example, a scanner may be used for this purpose that is similar to the AGILENT MICROARRAY SCANNER available from Agilent Technologies, Palo Alto, Calif. Other suitable apparatus and methods are described in U.S. patent application Ser. No. 09/846,125 "Reading Multi-Featured Arrays" by Dorsel et al.; and Ser. No. 09/430,214 "Interrogating Multi-Featured Arrays" by Dorsel et al.; which references are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing).

The above-described methods find use in a variety of different applications, where such applications are generally analyte detection applications in which the presence of a particular analyte in a given sample is detected at least qualitatively, if not quantitatively.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g. a member of signal producing system. Following sample preparation, the sample is first contacted with the first surface of the first substrate to produce a substrate supported sample, as described above, which product is then contacted with the array. The structure is positioned in a subject array assay device and a force is applied to the resultant structure, as reviewed above and the hybridization is performed under hybridization conditions, whereby complexes are formed between target nucleic acids that are complementary to probe sequences attached to the array surface. The presence of hybridized complexes is then detected. Specific hybridization assays of interest that may be practiced using the subject arrays include: gene discovery assays, differential gene expression analysis assays; nucleic acid sequencing assays, and the like. Patents describing methods of using arrays in various applications include U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

Where the arrays are arrays of polypeptide binding agents, e.g., protein arrays, specific applications of interest include analyte detection/proteomics applications, including those described in U.S. Pat. Nos. 4,591,570; 5,171,695; 5,436,170; 5,486,452; 5,532,128; and 6,197,599; as well as published PCT application Nos. WO 99/39210; WO 00/04832; WO 00/04389; WO 00/04390; WO 00/54046; WO 00/63701; WO 01/14425; and WO 01/40803; the disclosures of the United States priority documents of which are herein incorporated by reference.

The subject methods may also include pre-assembling or pre-packaging, i.e., pre-loading, a substrate having at least one array and/or a backing element in a subject array assay device at a first site, e.g., a manufacturing facility or the like, and transporting the pre-packaged array for use in an array assay to a remote or second site. By "second site" in this context is meant a site other than the site at which the array and/or backing element is pre-packaged in a subject array assay device. For example, a second site could be another site (e.g., another office, lab, etc.) in the same building, city, another location in a different city, another location in a different state, another location in a different country, etc. Usually, though not always, the first site and the second site are at least in different buildings, and may be at least one mile, ten miles, or at least one hundred miles apart. "Transporting" in this context refers to any means of getting the pre-packaged array and/or backing element from one site to the next, i.e., physically moving or shipping the pre-packaged array and/or backing element to a second site.

Once the array assay device with the array and/or backing element is pre-assembled or pre-packaged therein is received by a user at the second site, a sample may be contacted to a backing element (pre-package or not) and the backing element supported sample may then be contacted with an array (pre-packaged or not), where the order thereof may be reversed or otherwise altered as convenient for a given procedure. Next, the array assay device is closed and a force is applied to the backing element supported sample/array structure, as described above, to provide a substantially uniform distance between the backing element and the array substrate and an array assay, e.g., a hybridization assay, may be performed using the array assay device and pre-packaged array and/or pre-packaged backing element. Following completion of the array assay, the substrate having at least one array may be removed from the array assay device, positioned on an array scanner or reader and the at least one array may be scanned by the array reader to obtain a result, as described above.

The subject methods may include a step of transmitting data from at least one of the detecting and deriving steps, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, Internet, etc.

Kits

Finally, kits for use in practicing the subject methods are also provided. The subject kits at least include a cover, a base and clamping member for holding the cover to the base about a backing element/array assembly structure, as described above. For example, the systems may include a flexure clamping member and/or disk cover and/or flexure cover. The subject kits may also include one or more array assay assemblies, where each may include one or more arrays. The subject kits may also include one or more backing elements. The kits may further include one or more additional components necessary for carrying out an analyte detection assay, such as sample preparation reagents, buffers, labels, and the like. As such, the kits may include one or more containers such as vials or bottles, with each container containing a separate component for the assay, and reagents for carrying out an array assay such as a nucleic acid hybridization assay or the like. The kits may also include a denaturation reagent for the analyte, buffers such as hybridization buffers, wash mediums, enzyme substrates, reagents for generating a labeled target sample such as a labeled target nucleic acid sample, negative and positive controls.

In addition to the above components, the subject kits also typically include written instructions for practicing the subject methods. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, website, etc.

It is evident from the above discussion that the above described invention provides devices and methods for performing array assays which are simple to use, have minimal components, are relatively light weight, are inexpensive to manufacture and may be used with a multitude of different array formats. The above described invention provides for a number of advantages, including the provision of a substantially uniform distance between a backing element substrate and an array substrate, fluid loss prevention and the ability to test multiple samples with multiple arrays without cross-contamination. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An assay device comprising:
   (a) a base;
   (b) a cover;
   (c) a clamping member for holding said cover to said base, wherein said clamping member comprises:
      (i) a bridge comprising at least two extending arm portions that terminate in feet portions and a bore; and
      (ii) a rotatable screw disposed within said bridge; and
   (d) a flexure or spring element that interacts with said clamping member, wherein said assay device is configured such that upon actuation said clamping member applies a force to the cover and base in a manner sufficient to produce a substantially uniform distance between an array assembly and backing element along the entire length of the cover and base when said array assembly and backing element are present in said device, wherein said array assay device comprises at least one flexure.

2. The assay device of claim 1, wherein said at least one flexure is a separate component from said base and said cover.

3. The assay device of claim 2, wherein said at least one separate flexure is a clamping member flexure.

4. The assay device of claim 2, wherein said cover is said at least one flexure.

5. The assay device of claim 2, wherein said base is said at least one flexure.

6. The assay device of claim 1, wherein said device is configured to limit the travel of at least one of said base and said cover when they are operatively held together with said clamping member.

7. The assay device of claim 6, wherein said device further includes at least one of a spacer and a hardstop for limiting said travel.

8. The assay device of claim 7, wherein said device is configured to provide a compression force along the entire length of said at least one of said spacer and said hardstop to provide a substantially uniform capillary gap between said array assembly and said backing element.

9. The assay device of claim 1, wherein when said rotatable screw is actuated the screw contacts said cover.

10. The assay device of claim 1, wherein said arm portions comprise shoulders that allow flex upon actuation of said screw.

11. The assay device of claim 1, wherein said feet portions of said bridge contact an underside of said base when said clamping member is operatively positioned about said cover and said base.

* * * * *